(12) United States Patent
McMahen et al.

(10) Patent No.: US 8,512,759 B1
(45) Date of Patent: Aug. 20, 2013

(54) METHODS OF FORMULATING AND DESIGNING LIQUID DRUG SUSPENSIONS CONTAINING ION EXCHANGE RESIN PARTICLES

(75) Inventors: Russell McMahen, Flower Mound, TX (US); Mark Tengler, Colleyville, TX (US); Michael Sloane, Forth Worth, TX (US); Daniel Lockhart, Euless, TX (US)

(73) Assignee: Neos Therapeutics, LP, Grand Prairie, TX (US)

( * ) Notice: Subject to any disclaimer, the term of this patent is extended or adjusted under 35 U.S.C. 154(b) by 0 days.

(21) Appl. No.: 13/490,697

(22) Filed: Jun. 7, 2012

Related U.S. Application Data

(62) Division of application No. 12/985,340, filed on Jan. 5, 2011.

(60) Provisional application No. 61/292,420, filed on Jan. 5, 2010.

(51) Int. Cl.
*A61K 9/50* (2006.01)
*A61K 9/14* (2006.01)
*A61K 31/74* (2006.01)

(52) U.S. Cl.
USPC ............................ 424/501; 424/78.1; 424/486

(58) Field of Classification Search
USPC ........................................ 424/78.1, 486, 501
See application file for complete search history.

(56) References Cited

U.S. PATENT DOCUMENTS

| | | | |
|---|---|---|---|
| 2,990,332 A | 6/1961 | Keating | |
| 4,221,778 A | 9/1980 | Raghunathan | |
| 4,619,934 A | 10/1986 | Sunshine et al. | |
| 4,762,709 A * | 8/1988 | Sheumaker | 424/78.11 |
| 4,996,047 A | 2/1991 | Kelleher | |
| 4,999,189 A | 3/1991 | Kogan et al. | |
| 5,980,882 A | 11/1999 | Eichman | |
| 2003/0099711 A1 | 5/2003 | Meadows et al. | |
| 2004/0052849 A1 | 3/2004 | O'hare | |
| 2005/0013792 A1 * | 1/2005 | Hollenbeck et al. | 424/78.1 |
| 2006/0193877 A1 | 8/2006 | Tengler et al. | |
| 2007/0059270 A1 | 3/2007 | Hall et al. | |
| 2007/0140983 A1 | 6/2007 | Hall et al. | |
| 2007/0148239 A1 | 6/2007 | Hall et al. | |
| 2009/0011027 A1 | 1/2009 | Pathak et al. | |
| 2009/0176884 A1 | 7/2009 | Dickerson et al. | |

OTHER PUBLICATIONS

Prabhu et al. ("Comparison of Dissolution Profiles for Sustained Release Resinates of BCS Class I Drugs Using USP Apparatus 2 and 4: A Technical Note", AAPS PharmSciTech, vol. 9, No. 3, Sep. 2008).*
Hadzija et al. (Journal of Forensic Sciences 1996; 41(5):878-880).*
Prabhu et al., "Comparison of Dissolution Profiles for Sustained Release Resinates of BCS Class 1 Drugs Using USP Apparatus 2 and 4: A Technical Note", AAPS PharmSciTech, vol. 9, No. 3, Sep. 2008.
FDA's "Guidance for industry" (Jun. 14, 2006, pp. 1-35).

* cited by examiner

*Primary Examiner* — Aradhana Sasan
(74) *Attorney, Agent, or Firm* — Hunton & Williams LLP

(57) ABSTRACT

The invention relates to the formulation and quality control of liquid drug suspensions. In particular, the invention relates to methods of formulating liquid suspensions comprising drug-containing resin particles. The invention also relates to methods of confirming the acceptability of drug-containing resin particles for use in formulating liquid drug suspensions. The invention further relates to methods of formulating liquid suspensions in which drug-containing resin particles, the liquid suspension, or both are modified to achieve a desired in vitro dissolution profile. The invention also relates to a novel dissolution method and methods of predicting in vivo bioequivalence based on in vitro dissolution methods.

18 Claims, 14 Drawing Sheets

METHODS OF FORMULATING AND DESIGNING LIQUID DRUG SUSPENSIONS CONTAINING ION EXCHANGE RESIN PARTICLES

CROSS-REFERENCE TO RELATED APPLICATIONS

This application is a divisional application of U.S. application Ser. No. 12/985,340, filed Jan. 5, 2011, which claims priority to U.S. Provisional Patent Application No. 61/292,420, filed Jan. 5, 2010, the disclosures of which is hereby incorporated by reference in its entirety.

BACKGROUND OF THE INVENTION (a) Field of the Invention

The invention relates to the formulation and quality control of liquid drug suspensions for oral administration. In particular, the invention relates to methods of formulating liquid suspensions comprising drug-resin complex particles. The invention also relates to methods of confirming the acceptability of drug-resin complex particles for use in formulating liquid drug suspensions. The invention further relates to methods of formulating liquid suspensions in which drug-resin complex particles, the liquid suspension, or both are modified to achieve a desired in vitro dissolution profile. The invention also relates to a novel dissolution method and methods of predicting in vivo bioequivalence based on in vitro dissolution methods.

(b) Description of the Related Art

Sustained Released Liquid Drug Suspensions

Sustained- or prolonged-release dosage forms provide a controlled supply of drug to an organism over an extended period of time. Oral controlled-release drug preparations may provide the convenience of daytime dosing where the dosage form can be administered to an animal first thing in the morning and provide therapeutic levels of the drug throughout the day. Further, an oral controlled-release drug preparation may deliver drugs in a manner that will maintain therapeutically effective plasma levels in an mammal over a period of time that is significantly longer than that which is given by a typical drug dosage form. This eliminates the need to interrupt sleep to take medication and can prevent missed doses, thus improving patient compliance. Benefits obtained from such a controlled release of a specific drug include the control of cough, sleep, enuresis, pain and migraine headaches. Additionally, controlled release of antimicrobials can be used to treat or prevent infection.

Liquid oral dosage forms are known in the art. Liquid formulations have the distinct advantages of dosage flexibility and ease of swallowing. Moreover, there is a recognized need for sustained release formulations to be available in a convenient, easy-to-take liquid dosage form. However, the formulation of liquid oral suspensions having sustained-released capabilities has only resulted in limited success. In part, this is due to the challenges presented in maintaining the stability of sustained-release particles when present in liquid dispersal systems, and the difficulty in achieving sustained release of the drug from the dispersed phase.

Ion-Exchange Drug Resins

Ion-exchange technology has been an approach utilized for achieving sustained release for solid dosage forms and various attempts have been made to further utilize the technology in liquid suspension formulations as well. For example, U.S. Pat. No. 2,990,332 discloses a method of controlling the release rate of drug by adsorbing the salt form of a drug onto a carrier resin such as an ion-exchange resin. However, while complexing drugs on ion-exchange resins has been effective for taste-masking, such uncoated complexes provide only a relatively short delay of drug release and a poor control of drug release, because control of release rate is limited to variation in particle size and cross-linkage of the sulfonic acid-type resin used to prepare the adsorption compounds.

Another approach to prepare liquid suspensions having sustained-released capabilities is by coating drug resins with a water-permeable diffusion barrier. For example, U.S. Pat. No. 4,221,778 discloses a method for preparing products having controlled release properties involving a three-step process: (i) preparation of a drug-resin complex; (ii) treating this complex with a suitable impregnating agent; and (iii) coating the particles of treated complex with a water-permeable diffusion barrier. The impregnation agents are believed to act as humectants to stabilize the size of the swellable particle or minimize rupturing of the water-permeable diffusion barrier, and the barrier coating is believed to delay the release rate of the drug. U.S. Pat. Nos. 4,996,047 and 5,980,882 also provide drug-ion-exchange resin complex particles coated with a water-permeable diffusion barrier layer.

U.S. Pat. No. 4,762,709 discloses a formulation wherein a coated first drug/ion-exchange resin particle is suspended in a liquid carrier with an uncoated second drug/ion-exchange resin component bearing the same charge as the first drug in the coated first drug/ion-exchange resin particle. According to the reference, the release rate of the first drug from the coated first drug/ion-exchange resin particle is increased when the second drug is present in the second uncoated drug/ion-exchange resin complex compared to when the second drug is included with the first drug in the coated first drug/ion-exchange resin.

A product based on this ion-exchange technology is Tussionex® Pennkinetic® Extended-Release Suspension. Tussionex® drug suspension contains hydrocodone polistirex equivalent to 10 mg hydrocodone bitartrate and chlorpheniramine polistirex equivalent to 8 mg chlorpheniramine maleate. Tussionex® drug suspension was approved by the FDA in 1987.

Even though at least one liquid drug ion-exchange system was introduced over 20 years ago, very few products utilizing this technology exist in the market place. This is possibly due to (i) the poor suitability of the ion-exchange resin (i.e., hydrophobicity and swelling); (ii) the complex formulation and manufacturing processes that are required; and (iii) long term stability problems.

As such, there is a need in the art to develop sustained release liquid dosage forms and in particular, liquid dosage forms with better pharmacologic properties and stability that will appeal to the commercial marketplace. In particular, there remains a need for sustained release liquid dosage forms, suitable for once-a-day or twice-a-day administration of drugs.

Drug Development and Manufacturing

Drug development and manufacturing involves many processes including product design, product testing, quality control, and final product formulation. These processes are expensive, laborious, and time-consuming.

As such, there is a need in the art to simplify the processes of drug formulation design and quality control, and it would be useful to reduce the time and cost of performing these processes. In particular, there is also a need to develop quality control methods that ensure batches are efficiently and effectively reproduced. Likewise, there is a need to develop suitable methods for monitoring the effects of adjusting parameters in the development of liquid drug suspensions such as modifying particle size and coating of drug-containing resin particles and for qualifying drug-containing resin particles.

SUMMARY OF THE PREFERRED EMBODIMENTS OF THE INVENTION

The present invention addresses these needs by providing various methods of testing liquid drug suspensions and quality control of liquid drug suspensions. The invention also relates to methods of predicting in vivo bioequivalence based on in vitro dissolution methods.

In one embodiment, the invention provides a method of testing a drug suspension by comparing an in vitro dissolution profile for a test suspension comprising drug-resin complex particles to a control in vitro dissolution profile to determine whether the test suspension in vitro dissolution profile matches the control in vitro dissolution profile. The in vitro dissolution assay is performed using a test suspension comprising drug-resin complex particles to generate a test in vitro dissolution profile, where there is a pre-determined hold period between the formation of the test drug suspension and initiation of the dissolution assay for the test drug suspension. The test in vitro dissolution profile is then compared to a control in vitro dissolution profile that correlates to a target in vivo profile, and which generated by an in vitro dissolution assay for a control drug suspension, where there is a similar pre-determined hold period between the formation of the control drug suspension and initiation of the dissolution assay for the control drug suspension. The pre-determined hold period between the formation of the test drug suspension and initiation of the dissolution assay for the test drug suspension, and the similar pre-determined hold period for the control drug suspension are substantially less than a period necessary for a drug suspension to fully age, and will be considered substantially identical so long as the properties of the drug suspensions do not change substantially during the time between the shorter and the longer of the two lag periods. Suitable pre-determined hold periods substantially less than a period necessary for a drug suspension to fully age may be about or less than 14 days, 13 days, 12 days, 11 days, 10 days, 9 days, 8 days, 7 days, 6 days, 5 days, 4 days, 3 days, 2 days, 1 day, 20 hours, 16 hours, 12 hours, 10 hours, 8 hours, or 4 hours.

In an alternative embodiment, the dissolution assay for the test drug suspension is initiated promptly after the formation of the test drug suspension, and the dissolution assay for the control drug suspension is initiated promptly after the formation of the control drug suspension. In a particular embodiment, the dissolution assay of the test drug suspension and the dissolution assay of the control drug suspension are initiated after substantially identical lag periods. Lag periods for this embodiment may be of the same duration as the pre-determined hold periods described above.

In another embodiment, the drug-resin complex particles may be modified if the test suspension in vitro dissolution profile does not match the control in vitro dissolution profile. In a particular embodiment, the method further comprises modifying the drug-resin complex particles to form modified drug-resin complex particles and combining the modified drug-resin complex particles with a plurality of excipients in a liquid carrier to form a liquid test drug suspension, and comparing an in vitro dissolution profile of this test suspension to a control in vitro dissolution profile. In particular embodiments, the drug-resin complex may be modified by, for example, increasing the weight of coating on the drug-resin complex particle, modifying the size of the drug-resin complex particle, or modify the amount of drug loaded above or below the holding capacity on said drug-resin complex particle to modify the rate of dissolution of the test suspension.

In another embodiment, the test drug suspension may be modified if the test suspension in vitro dissolution profile does not match the control in vitro dissolution profile. In a particular embodiment, the method comprises modifying the test drug suspension to form a modified test drug suspension and comparing an in vitro dissolution profile of the modified test suspension to a control in vitro dissolution profile. In particular embodiments, the test suspension may be modified, for example, by altering the ionic strength of the test drug suspension or altering the active resin-site balance.

In another embodiment, the invention provides a method for confirming the acceptability of a quantity of drug-resin complex particles by comparing an in vitro dissolution profile of a test suspension comprising a sample of the quantity of drug-resin complex particles to control in vitro dissolution profile and accepting or rejecting the quantity of drug-resin complex particles based on this comparison.

In another embodiment, the invention provides for a method of formulating a liquid drug suspension comprising suspending drug-contain resin particles in a liquid suspension, the drug-containing resin particles comprising a first plurality of particles comprising a water-permeable coating and a second plurality of uncoated particles, and the first and second plurality of particles containing the same drug. In a preferred embodiment, the liquid drug suspension provides for early onset of therapeutic effect, while masking the taste of the drug and maintaining bioequivalence and bioavailability, or efficacy, for an extended period.

In another particular embodiment, the invention provides for an extended release liquid drug suspension that is bioequivalent to Tussionex® drug suspension. In a preferred embodiment, the liquid drug suspension has a tighter particle size distribution and lower batch-to-batch variability than Tussionex® drug suspension.

In yet another embodiment, the invention provides for a method of making a liquid drug suspension that is bioequivalent to Tussionex® drug suspension. In one embodiment, the method comprises dispersing xanthan gum prior to hydration.

DETAILED DESCRIPTION OF PREFERRED EMBODIMENTS OF INVENTION

Figure 1:
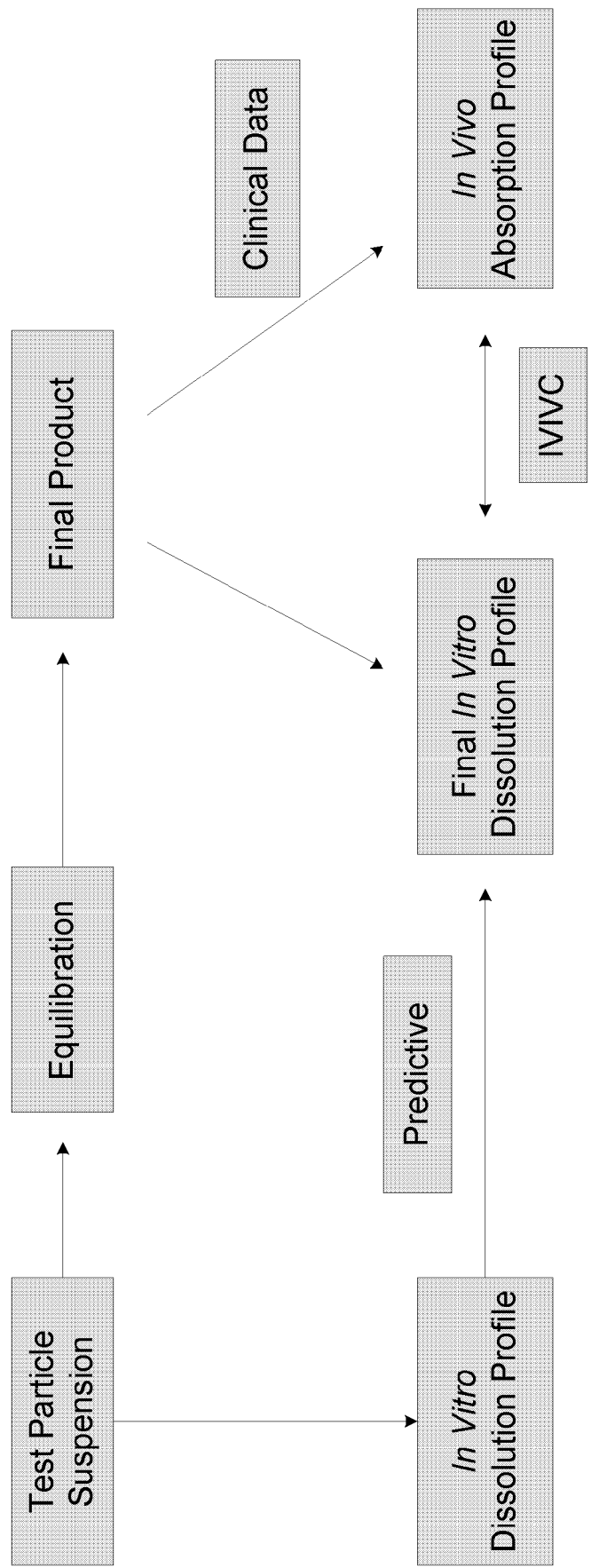
FIG. 1 depicts a method of obtaining an in vitro dissolution profile of a liquid drug suspension which correlates with in vivo performance.

Solid drug dosages are generally stable until the drug product is administered to a patient. On the other hand, liquid drug products are more likely to undergo chemical reactions during storage periods between manufacture and administration. The present inventors have discovered that extended release products, where the drug is sequestered by binding to an ion exchange material, are particularly susceptible to this phenomenon. In fact, when using ion exchange resins to ionically bind a drug, any formulations where the ion exchange resin has free sites are initially likely to be thermodynamically unstable, and if such a formulation is in the form of a liquid suspension, thermodynamics will drive changes in the amount and location of bound drug during storage until the system reaches a thermodynamically stable equilibrium. During the period that the approach to equilibrium is proceeding, the release profile for the drug will change over the time period.

While a liquid drug product typically reaches a stable equilibrium by the time it is administered to a patient due to the time lag accompanying distribution after manufacture, the manufacturer is not as lucky as the patient. Changes in the relative amounts of different forms of the drug (e.g., bound/unbound, sequestered behind semi-permeable membranes, etc.) are likely to occur for some time after manufacture of a liquid drug suspension. The manufacturer can, of course, suspend any product testing until the product reaches equilibrium. However, the present inventors have devised an alternative method to avoid the delay in processing that would be occasioned by a wait for equilibration. The methods of this invention permit manufacturers who need to obtain information about the drug resin complex to assay liquid drug suspensions promptly after manufacture and still obtain information that is consistent with the behavior of a completely equilibrated (i.e., "fully aged") product.

The invention provides for various methods of formulating oral liquid suspensions comprising drug-containing ion-exchange resin particles. Methods of formulating such products generally comprise the following steps: (a) designing/obtaining drug-containing resin particles; (b) suspending the drug-containing resin particles into a suspension preparation; (c) introducing an aliquot of the suspension preparation into a dissolution medium and producing a test in vitro dissolution profile by determining the concentration of drug in the dissolution medium; (d) comparing said test in vitro dissolution profile to a control in vitro dissolution profile, obtained from a control liquid drug suspension, that correlates to a target in vivo profile. If the test in vitro dissolution profile matches the control dissolution profile, then the suspension preparation will be suitable for final formulation. If the test in vitro dissolution profile does not match the control dissolution profile, then the drug-containing resin particles, the suspension preparation, or both may be modified. The suspension preparation and/or the control liquid drug suspension may be substantially similar in physicochemical characteristics to a finally formulated and fully aged suspension. The invention provides for various quality control methods using these steps and modifications thereof.

The inventors have observed that a fully aged liquid formulation comprising drug-containing ion-exchange resin particles can be used to determine whether the formulation will correspond to a desired in vivo serum concentration profile. In a particular example, the inventors prepared a liquid formulation comprising drug-containing ion-exchange resin particles and allowed this formulation to fully age (e.g., held in suspension until thermodynamic stability was reached, approximately one month). An in vitro dissolution assay was performed using an aliquot of the fully aged suspension. This fully aged suspension was then administered to subjects, and it was determined that the suspension was bioequivalent to an FDA approved drug based on in vivo serum concentration profiles obtained from the subjects. The inventors then established a in vitro/in vivo correlation (IVIVC) between the in vitro dissolution profile of the fully aged suspension and the in vivo serum concentration profile, and demonstrated that the in vitro dissolution profile of a fully aged suspension can be used to determine whether a liquid formulation will correspond to a desired in vivo serum concentration profile. A schematic of this process is shown in the top line and right hand side of FIG. 1. It will be understood that the fully aged suspension used in such studies is preferably substantially similar in physicochemical characteristics to a finally formulated and fully aged suspension product. As such, the fully aged suspension used in such studies need not, for example, include dyes or flavorings.

Figure 2:
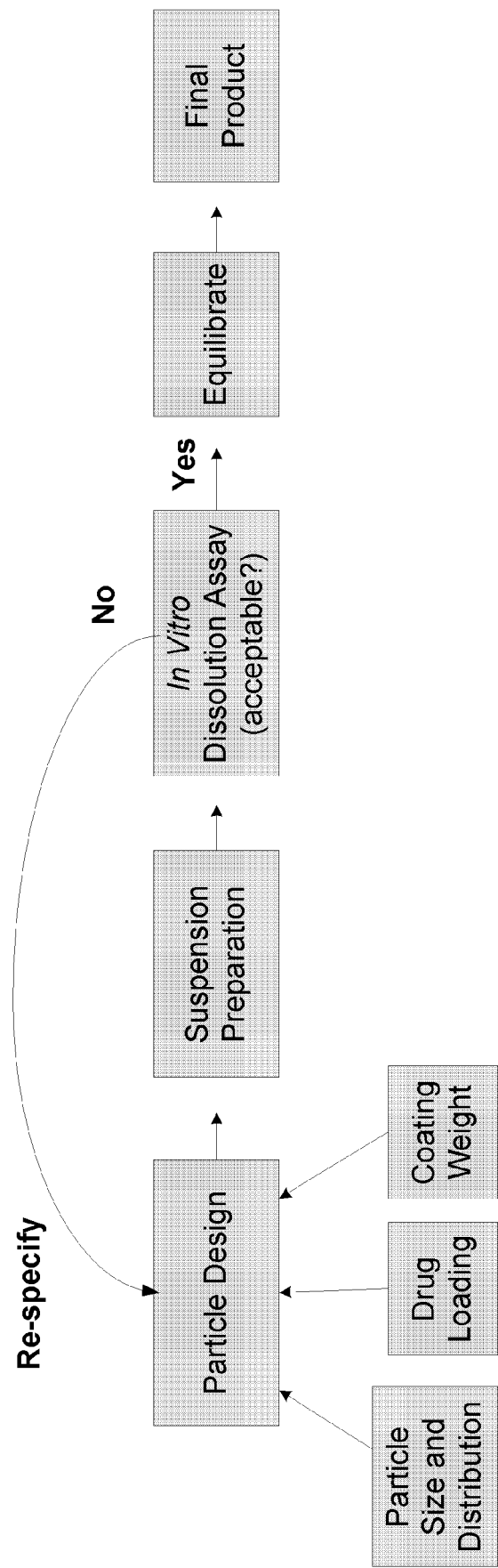
FIG. 2 depicts a method of using a prompt dissolution assay to refine drug-containing resin particles.
Figure 3:
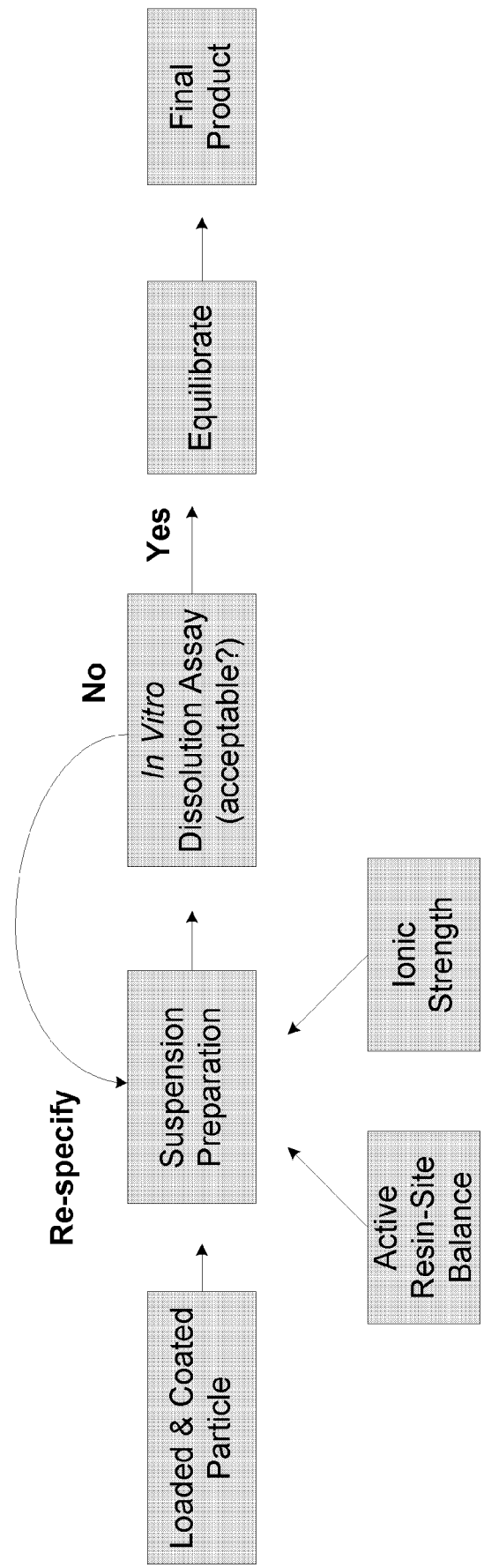
FIG. 3 depicts a method of using a prompt dissolution assay to refine a liquid drug suspension.

The inventors then surprisingly discovered that it is not necessary to wait for the period required to obtain a fully aged liquid drug formulation before determining whether the formulation will correspond to a desired in vivo serum concentration profile. Indeed, the inventors discovered that during the process of designing or manufacturing a liquid drug formulation, the drug-containing ion-exchange resin particles and/or the liquid drug suspension can be monitored or tested to ensure quality and/or a desired drug release profile or absorption profile without waiting for the liquid drug suspension to fully age. In particular, the inventors determined that an in vitro dissolution assay may be performed on a test suspension promptly after making a liquid drug formulation. The in vitro dissolution profile obtained from this prompt assay is then compared to an in vitro dissolution profile of a control suspension obtained by a similar prompt assay and which has been correlated to a desired in vivo serum concentration profile. (See left hand side and lower line of FIG. 1). When performing the prompt dissolution assays for the test and control suspensions, aliquots of the test and control suspensions are collected and tested for dissolution profiles after the same lag period from completion of the suspension. If the in vitro dissolution profile of the test suspension does not match the in vitro dissolution profile of the control suspension, then modification of (1) the drug-containing ion-exchange resin particles (see FIG. 2); (2) the liquid drug suspension (see FIG. 3); or (3) both drug-containing ion-exchange resin particles and the liquid drug suspension may be undertaken to achieve the desired in vitro dissolution profile.

The inventors observed that a suitable period of time (e.g., approximately one month) was necessary to achieve a thermodynamically stable suspension. The inventors observed that after a liquid drug suspension comprising drug-containing ion-exchange resin particles is formulated, the suspension becomes more stable as time passes until it reaches a thermodynamic stability. The present inventors determined that in vitro dissolution profiles obtained from time periods substantially less than a period necessary for a drug suspension to fully age can be correlated with an in vitro dissolution profile of a fully aged drug suspension that, in turn, has been correlated with a desired in vivo serum concentration profile. As such, the inventors have determined that in vitro dissolution profiles obtained promptly (i.e., from time periods substantially less than a period necessary for a drug suspension to fully age) can be predictive of desired in vivo serum concentration profiles. This surprising discovery will significantly reduce time and cost for designing liquid drug formulations.

DEFINITIONS

As used herein, "finally formulated" means a suspension that includes all of the components typically formulated for commercial distribution such as stabilizers, thickeners, dyes, flavorants, etc. As used herein, "substantially similar in physicochemical characteristics" means a suspension having the same colligative and ionic (e.g., pH) properties, viscosity, and specific gravity. These properties may be measured by methods known in the art.

As used herein, "fully aged" means a liquid suspension that is stable to time-dependent changes in release profiles. As used herein, "a period necessary for a drug suspension to fully age" means a time period after preparation of a liquid suspension sufficient for the suspension to become stable. In particular, for a fully aged suspension, all chemical forms or states of the drug (e.g., bound/unbound, ionized/unionized, on one side of a semi-permeable membrane or the other, etc.) are in equilibrium with each other. As used herein, "finally formulated and fully aged suspension product" means a product that is suitable for commercial distribution.

As used herein, "control" drug preparations are pharmaceutically active compositions which have been shown to be efficacious in vivo, preparations having the same composition as a preparation which has demonstrated in vivo efficacy, preparations which have been shown to be bioequivalent to a reference listed drug, or preparations having the same composition as a preparation which has demonstrated bioequivalence to a reference listed drug. A control in vitro dissolution profile may be generated using a control drug preparation or a preparation of the same drug with substantially similar physico-chemical characteristics to the control drug preparation.

As used herein, a dissolution profile is "equivalent" to another profile if the f2 similarity factor calculated for the two profiles is greater than or equal to 50. (See Moore and Flanner, Pharm. Tech. 20: 64-74, 1996). As used herein, two dissolution profiles "match" if they are equivalent or if one falls within pharmaceutically acceptable limits, typically 80% to 125%, of the other, directly, or indirectly through a predetermined mathematical relationship (e.g., using information correlated for different lag times).

As used herein, an "early onset of therapeutic effect" relates to specified amount of drug released within a shortened timeframe (i.e., have more Area Under Curve (AUC) initially), but still passes f2 testing. For example, the invention contemplates the release of at least 15% more of the drug within the first 15, 30, 60, 75, or 90 minutes of administration, as compared to conventional oral dosage forms of the same drug. An "early onset of therapeutic effect" is contrasted with "dose dumping," which is the premature and exaggerated release of a drug that produces adverse effects or toxicity.

As used herein, an assay is "prompt" or it is performed "promptly" if it is performed on a newly manufactured suspension before the suspension reaches equilibrium. An assay may be considered prompt even though there is a predetermined hold period or lag time between manufacture of a suspension and its assay. In particular, prompt assays are likely to be performed no more than two weeks after manufacture of a suspension is completed, preferably after a lag time of no more than three days, more preferably no more than 24 hours. Two comparable assays are both performed promptly if the lag period between them differs by less than 20% or if the properties of the drug suspensions do not change appreciably in the difference between their lag periods. Predetermined hold times for such "prompt" assays are considered substantially identical.

Drug-Resin Complex Particles

The invention provides for various methods of product formulation and assays involving drug-containing resin particles. These particles comprise at least one pharmacologically active drug bound to particles of an ion-exchange resin to provide a drug-resin complex. These drug-resin complex particles may be coated with a water-permeable diffusion barrier coating that is insoluble in gastrointestinal fluids thereby providing a controllable sustained release of drug under conditions encountered in the gastrointestinal tract. The particles may also include an enteric coating. Drugs are typically bound to the resin particles by ionic bonds. The drug-resin complex particles may also contain unbound drug or drugs bound by non-ionic means.

Resins

Ion-exchange resins suitable for use in the preparations and methods described herein are water-insoluble and comprise a pharmacologically inert organic and/or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g., modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion-exchangers suitable for use in ion-exchange chromatography and for such applications as deionization of water are suitable for use in the controlled release of drug preparations. Suitable ion exchange resins are also sold under the trade names Amberlite and Dowex. Such ion-exchangers are described by H. F. Walton in "Principles of Ion Exchange" (pp. 312-343) and "Techniques and Applications of Ion-Exchange Chromatography" (pp. 344-361) in Chromatography. E. Heftmann, editor), Van Nostrand Reinhold Company, New York (1975), incorporated herein by reference. Exemplary ion-exchange resins that can be used in the present invention have exchange capacities below about 6 milliequivalents (meq)/gram and preferably below about 5.5 meq/gram.

Typically, the size of the ion-exchange particles is from about 30 microns to about 500 microns, preferably the particle size is within the range of about 40 micron to about 150 micron for liquid dosage forms, although particles up to about 1,000 micron can be used for solid dosage forms, e.g., tablets and capsules. Particle sizes substantially below the lower limit are difficult to handle in all steps of the processing. Commercially-available ion-exchange resins having an irregular shape and larger diameters up to about 200 micron, are gritty in liquid dosage forms and have a greater tendency to fracture when subjected to drying-hydrating cycles. Moreover, it is believed that the increased distance that a displacing ion must travel in its diffusion into these large particles, and the increased distance the displaced drug must travel in its diffusion out of these large particles, cause a measurable but not readily controlled prolongation of release, even when the drug-resin complexes are uncoated. Release of drug from uncoated drug-resin complexes with particle sizes in the approximate range of 40 micron to 150 micron is relatively rapid in the appropriate environment. Satisfactory control of the release from such complexes is achieved almost exclusively by the applied diffusion barrier coating.

Both regularly and irregularly shaped particles may be used as resins. Regularly shaped particles are those particles that substantially conform to geometric shapes, such as spherical, elliptical, cylindrical and the like, which are exemplified by Dow XYS-40010.00 and Dow XYS-40013.00 (The Dow Chemical Company). Irregularly shaped particles are all particles not considered to be regularly shaped, such as particles with amorphous shapes and particles with increased surface areas due to surface channels or distortions. Irregularly shaped ion-exchange resins of this type are exemplified by Amberlite IRP-69 (Rohm and Haas). Two of the preferred resins of this invention are Amberlite IRP-69 and Dow XYS-40010.00. Both are sulfonated polymers composed of polystyrene cross-linked with 8% of divinylbenzene, with an ion-exchange capacity of about 4.5 to 5.5 meq/g of dry resin ($Na^+$-form). Their essential difference is in physical form. Amberlite IRP-69 consists of irregularly-shaped particles with a size range of 47 micron to 149 micron produced by milling the parent large-sized spheres of Amberlite IRP-120. The Dow XYS-40010.00 product consists of spherical particles with a size range of 45 micron to 150 micron. Another useful exchange resin, Dow XYS-40013.00, is a polymer composed of polystyrene cross-linked with 8% of divinylbenzene and functionalized with a quaternary ammonium group; its exchange capacity is normally within the range of approximately 3 to 4 meq/g of dry resin.

The following U.S. Patents and Publications describe resins suitable for use in the preparations and methods described herein: U.S. Pat. Nos. 4,221,778; 4,996,047; and 5,980,882; U.S. Publication Nos. 2003/0099711; 2006/0193877; 2007/0059270; 2007/01400983; 2007/0148239; and 2009/0011027. The disclosure of each of these patents and publications is incorporated by reference herein in their entireties.

As described herein, one of skill in the art may modify the resin particle size to modify a drug release profile and ultimately achieve a desired in vivo serum concentration profile.

Drugs

Drugs that are suitable for use in these preparations include drugs for the treatment of respiratory tract disorders such as, for example, antitussive expectorants such as dihydrocodeine phosphate, codeine phosphate, noscapine hydrochloride, phenylpropanolamine hydrochloride, potassium guaiacolsulfonate, cloperastine fendizoate, dextromethorphan hydrobromide and chloperastine hydrochloride; bronchodilators such as dl-methylephedrine hydrochloride and dl-methylephedrine saccharinate; and antihistamines such as fexofenadine HCl or di-chlorpheniramine maleate. Other drugs useful for the invention include drugs for the treatment of digestive tract disorders such as, for example, digestive tract antispasmodics including scopolamine hydrobromide, metixene hydrochloride and dicyclomine hydrochloride, drugs for the treatment of central nervous system disorders such as, for example, antipsychotic drugs including phenothiazine derivatives (chlorpromazine hydrochloride, etc.) and phenothiazine-like compounds (chlorprothixene hydrochloride, etc.), antianxiety drugs such as benzodiazepine derivatives (chlordiazepoxide hydrochloride, diazepam, etc.), antidepressants such as imipramine compounds (imipramine hydrochloride, etc.), antipyretic analgesics such as sodium salicylate, and hypnotics such as phenobarbital sodium; opioid analgesic drugs such as alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dirnethylthiambutene, dioxaphetyl butyrate, dipipanone, eptazocine, ethoheptazine, ethylmethylthiambutene, ethylmorphine; etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, nounorphine, norpipanone, opium and compounds contained therein, oxycodone, oxymorphone, papavreturn, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like; and drugs for the treatment of respiratory system disorders such as, for example, coronary dilators including etafenone hydrochloride, antiarrhythmics such as procainamide hydrochloride, calcium antagonists such as verapamil hydrochloride, hypotensive drugs such as hydrazine hydrochloride, propranolol hydrochloride and clonidine hydrochloride, and peripheral vasodilators/vasoconstrictors such as tolazoline hydrochloride. Antibiotics may also be useful such macrolides such as oleandomycin phosphate, tetracyclines such as tetracycline hydrochloride, streptomycins such as fradiomycin sulfate, and penicillin drugs such as dicloxacillin sodium, pivmecillinam hydrochloride and carbenicillinindanyl sodium. Chemotherapeutic drugs may also be used including sulfa drugs such as sulfisomidine sodium; antituberculosis drugs such as kanamycin sulfate, and antiprotozoan drugs such as amodiaquine hydrochloride. An excellent sustained releasing effect is obtained in basic drugs for the respiratory tract such as dihydrocodeine phosphate, di-methyl-ephedrine hydrochloride and phenylpropanolamine hydrochloride. The following U.S. Patents and Publications describe drugs suitable for use in the preparations and methods described herein: U.S. Pat. Nos. 4,221,778; 4,996,047; and 5,980,882; U.S. Publication Nos. 2003/0099711; 2006/0193877; 2007/0059270; 2007/01400983; 2007/0148239; and 2009/0011027. The disclosure of each of these patents and publications is incorporated by reference herein in their entireties.

Alternatively, drugs that are suitable for the invention may be acidic, basic or amphoteric. Acidic drugs that can be used in the present invention include, for example, dehydrocholic acid, diflunisal, ethacrynic acid, fenoprofen, furosemide, gemfibrozil, ibuprofen, naproxen, phenytoin, probenecid, sulindac, theophylline, salicylic acid and acetylsalicylic acid. Basic drugs that can be used in the present invention include, for example, acetophenazine, amitriptyline, amphetamine, benztropine, biperiden, bromodiphenhydramine, brompheniramine, carbinoxamine, chloperastine, chlorcyclizine, chlorpheniramine, chlorphenoxamine, chlorpromazine, clemastine, clomiphene, clonidine, codeine, cyclizine, cyclobenzaprine, cyproheptadine, desipramine, dexbrompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levopropoxyphene, maprotiline, meclizine, mepenzolate, meperidine, mephentermine, mesoridazine, methadone, methylephedrine, methdilazine, methscopolamine, methysergide, metoprolol, nortriptylene, noscapine, nylindrin, orphenadrine, papaverine, pentazocine, phendimetrazine, phentermine, phenylpropanolamine, pyrilamine, tripelennamine, triprolidine, promazine, propoxyphene, pro panolol, pseudoephedrine, pyrilamine, quinidine, scopolamine, dextromethorphan, chlorphenitarraizae and codeine. Amphoteric drugs that can be used in the present invention include, for example, aminocaproic acid, aminosalicylic acid, hydromorphone, isoxsuprine, levorphanol, melphalan, morphine, nalidixic acid, and paraaminosalicylic acid.

Preferably, drugs which may be used in the invention include drugs for the indication of attention-deficit/hyperactivity disorder (ADHD) such as methylphenidate, amphetamine and dextroamphetamine, dexmethylphenidate, and clonidine; drugs for the indication of gastroesophageal reflux disease (GERD) such as ranitidine hydrochloride, omeprazole, lansoprazole, raberprazole sodium; drugs for the indication of bacterial infections such as tetracylcine, clindamycin, erythromycine ethylsuccinate, sulfamethoxazole and trimethoprim, clarithromycin, ciprofloxacin; drugs for the indication of chickenpox such as acylovir; drugs for the indication of allergic rhinitis such as fexofenadine and fexofenadine/pseudoephedrine; drugs for the indication of antitussive/antihistimine such as hydrocodone-chlorpheniramine and codeine-chlorpheniramine; drugs for the indication of antitussives such as promethazine, promethazine with codeine, promethazine with dextromethorphan, benzonatate, potassium guaiacol sulfonate, hydrocodone-homatropine, hydrocodone-guaifenesin, codeine-pseudoephedrine, and codeine-guaifenesin; drugs for the indication of epilepsy such as levetiracetam, gabapentin, carbamazepine, topiramate, and baciofen; drugs for the indication of epilepsy/biolar such as lamotrigine and valproate sodium; drugs for the indication of Alzheimer's such as galantamine hydrobromide, rivastigmine tartrate, and donepezil hydrochloride; drugs for the indication of multiple sclerosis such as tizanadine; drugs for the indication of Parkinson's such as carbidopa-levodopa, ropinirole hydrochloride, and pramipexole dihydrochloride; drugs for the indication of bipolar disorder such as quetiapine fumarate, lithium carbonate, and perphenazine; drugs for the indication of anxiety such as hydroxyzine; drugs for the indication of depression such as venlafaxine hydrochloride; drugs for the indication of moderate/severe pain such as morphine (sulfate), oxycodone, oxycodone/acetaminaphen, hydroorphone, tramadol hydrochloride, hydrocodone/acetaminaphen, and codeine; drugs for the indication of trigeminal neuralgia such as carbamazepine; and drugs for the indication of muscle spasms such as cyclobenzapine.

The compositions of this invention may optionally contain one or more other known therapeutic agents, particularly those commonly utilized in cough/cold preparations, such as, for example, a decongestant such as pseudoephedrine hydrochloride, phenylpropanolamine HCl, phenylephrine hydrochloride and ephedrine hydrochloride; an analgesic such as acetaminophen and ibuprofen; an expectorant or mucolytic such as glyceryl guaiacolate, terpin hydrate, ammonium chloride, N-acetylcysteine and ambroxol; an antihistamine such as chlorpheniramine maleate, doxylamine succinate, brompheniramine maleate and diphenhydramine hydrochloride; an antitussive such as promethazine, promethazine with codeine, promethazine with dextromethorphan, benzonatate, hydrocodone-homatropine, hydrocodone-guaifenesin, codeine-pseudoephedrine, and codeine-guaifenesin; and an antitussive/antihistimine such as hydrocodone-chlorpheniramine and codeine-chlorpheniramine. See, e.g., U.S. Pat. No. 4,619,934, which is incorporated by reference herein. Also useful are bronchodilators such as theophylline and albuterol.

Drug-Resin Complexes

Binding of drug to resin can be accomplished using methods known in the art. Indeed, one of ordinary skill in the art can easily determine the appropriate method depending upon the drug. Typically four general reactions are used for a basic drug, these are: (a) resin (Natform) plus drug (salt form); (b) resin ($Na^+$-form) plus drug (as free base); (e) resin ($H^+$-form) plus drug (salt form); and (d) resin ($H^+$-form) plus drug (as free base). All of these reactions except (d) have cationic by-products and these by-products, by competing with the cationic drug for binding sites on the resin, reduce the amount of drug bound at equilibrium. For basic drugs, stoichiometric binding of drug to resin is accomplished only through reaction (d). Without being limited by theory, it is believed that the extent of drug binding is critical to the maintenance of the integrity of the diffusion barrier coating.

Four analogous binding reactions can be carried out for binding an acidic drug to an anion exchange resin. These are: (a) resin (Cl⁻-form) plus drug (salt form); (b) resin (Cl⁻-form) plus drug (as free acid); (c) resin (OH⁻-form) plus drug (salt form); and (d) resin (OH⁻-form) plus drug (as free acid). All of these reactions except (d) have ionic by-products and the anions generated when the reactions occur compete with the anionic drug for binding sites on the resin with the result that reduced levels of drug are bound at equilibrium. For acidic drugs, stoichiometric binding of drug to resin is accomplished only through reaction (d). The binding may be performed, for example, as a batch or column process, as is known in the art. The drug-resin complexes may be prepared by a batch process that is based on reaction (d). The drug-resin complex thus formed is collected by filtration and washed with deionized or purified water to ensure removal of any unbound drug. The complexes are usually air-dried in trays at from 25 to 60° C.

Drug-resin complexes rapidly release the drug in the patient, such as, for example, in the gastrointestinal tract. For example, an Amberlite IR-120 phenylpropanolamine complex with a 35 percent drug loading released 61 percent of drug in 60 minutes in a 0.1 N hydrochloric acid dissolution medium.

The amount of drug that can be loaded onto a resin will typically range from about 1% to about 80%, preferably about 15% to about 60%, by weight of the loaded drug-resin particles. A skilled artisan with little or no experimentation can readily determine the optimum loading for any drug resin complex. In a preferred embodiment, loadings of about 30% to about 60% by weight of the drug-resin particles can be employed.

The following U.S. Patents and Publications describe drug-resin complexes suitable for use in the preparations and methods described herein: U.S. Pat. Nos. 4,221,778; 4,996, 047; and 5,980,882; U.S. Publication Nos. 2003/0099711; 2006/0193877; 2007/0059270; 2007/01400983; 2007/0148239; and 2009/0011027. The disclosure of each of these patents and publications is incorporated by reference herein in their entireties.

As described herein, one of skill in the art may increase or decrease the amount of drug loaded on a resin particle to modify a drug release profile and ultimately achieve a desired in vivo serum concentration profile.

Impregnation

Drug-resin particles can be impregnated with a humectant substantially as described in U.S. Pat. No. 4,221,778. The humectant can be added as an ingredient in the resin drug complexation step or preferably, the particles can be treated with the humectant after complexing. This treatment helps particles retain their geometry, and enables the effective application of diffusion barrier coatings to such particles. One preferred humectant is polyethylene glycol, a hydrophilic agent. Other effective humectant agents include, for example, propylene glycol, lactose, methylcellulose, hydropropylmethylcellulose, sugar alcohols such as sorbitol, mannitol, polyvinylpyrrolidone, carboxypolymethylene, xanthan gum, propylene glycol, alginate and combinations of these agents. The humectant may be added in an amount of up to about 50 parts by weight of the resin or 50 to 150 parts by weight of the resin; such humectant levels have been found to be effective. Preferably, the humectant (solvating agent) is added in an amount of about 75 to about 100 parts by weight of resin. Such pretreatment of drug-resin complex enables the effective use of diffusion barrier coatings, resulting in the ability to effectively prolong the release of drugs from drug-resin complexes.

Diffusion Barrier Coating

Next, loaded particles may be coated with a diffusion barrier comprising a water-permeable, film-forming polymer. Any coating procedure which provides a contiguous coating on each particle of drug-resin complex without significant agglomeration of particles may be used. Coatings may be applied with a fluid-bed coating apparatus having the Wurster configuration. Measurements of particle size distribution can be done before and after coating to show that agglomeration of particles is insignificant.

The polymer may be any of a large number of natural or synthetic film-formers used singly, or in admixture with each other, and optionally in admixture with plasticizers, pigments and other substances to alter the characteristics of the coating. In general, the coating should be insoluble in and permeable to water. The water-permeable barrier comprises a pharmaceutically acceptable polymer such as, for example, ethylcellulose, methylcellulose, hydroxypropylmethylcellulose (HPMC), hydroxyethlycellulose (HEC), acrylic acid ester, cellulose acetate phthalate, HEC phthalate, HPMC phthalate or other cellulosic polymers, or mixtures of polymers. Additional examples of coating polymers are described by R. C. Rowe in Materials. Used in Pharmaceutical Formulation (A. T. Florence, editor), Blackwell Scientific Publications, Oxford, 1-36 (1984), incorporated by reference herein. Preferably the diffusion barrier is ethyl cellulose, for example, an ethyl cellulose having the content of ethoxyl group from 44 to 47.5%, preferably from 45 to 46.5%. In embodiments of the present invention, the inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticizer the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such a dibutyl sebacate, diethyl phthalate, tributyl citrate and triacetin, although it is possible that other water-insoluble plasticizers (such as acetylated monoglycerides, phthalate esters, castor oil, etc.), or water-soluble plasticizers may be used. A plasticizer such as Durkex 500 vegetable oil may also be incorporated to improve the film forming property. In one alternative, it is desirable to incorporate a water-soluble substance, such as methyl cellulose, to alter the permeability of the coating.

One commercially available aqueous dispersion of ethylcellulose is Aquacoat® (FMC Corp., Philadelphia, Pa., U.S.A.). Aquacoat® is typically prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is preferable to intimately mix the Aquacoat® with a suitable plasticizer prior to use.

Another aqueous dispersion of ethylcellulose is commercially available as Surelease® (Colorcon, Inc., West Point, Pa., U.S.A.). This product is typically prepared by incorporating plasticizer into the dispersion during the manufacturing process. A hot melt of a polymer, plasticizer (e.g., dibutyl sebacate), and stabilizer (e.g., oleic acid) may be prepared as a homogeneous mixture, which is then diluted with an alkaline solution to obtain an aqueous dispersion which can be applied directly onto substrates.

Another alternative coating material is a mixture of an insoluble film forming polymer and a water soluble pore former or polymer. One preferred water soluble polymer is methyl cellulose.

The barrier coating materials can be applied as an aqueous suspension. Optimum coat weight and coat thickness may be determined for each drug-resin complex and generally depend on the drug release characteristics of the resin for a particular drug. For example, for drug release times within about 1 hour to about 4 hours, the drug-resin complex may be coated with a light coat weight. A light coat weight is a coat weight present in the amount of about 10% to about 20% by weight of the dry resin. For drug release times from about 6 hours to 10 hours, a medium coat weight may be used, i.e. a coat weight present in the amount of 30% to about 35% by weight. For drug release times for about 12 hours, a heavy coat weight may be used, i.e. a coat weight of about 40% to 50% by weight of the dry resin. Typically, the water-permeable, film-forming polymer comprises from about 1% to about 60% by weight of the drug-resin complex, and preferably from about 20% to about 50% by weight of the dry resin. In terms of coat thickness, preferably, the diffusion barrier coat thickness is at least 5 microns and more preferably, the diffusion barrier coat thickness is from about 10 microns to about 50 microns.

The following U.S. Patents and Publications describe coating materials suitable for use in the preparations and methods described herein: U.S. Pat. Nos. 4,221,778; 4,996,047; and 5,980,882; U.S. Publication Nos. 2003/0099711; 2006/0193877; 2007/0059270; 2007/01400983; 2007/0148239; and 2009/0011027. The disclosure of each of these patents and publications is incorporated by reference herein in their entireties.

As described herein, one of skill in the art may increase or decrease the amount of coating, or change the composition of the coating, applied to a resin particle to modify a drug release profile and ultimately achieve a desired in vivo serum concentration profile.

Liquid Drug Suspensions

Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. Liquid forms, such as syrups and suspensions, preferably contain from about 1% to about 50%, and more preferably from about 1% to about 25%, and most preferably from about 3% to about 10%, of the drug-resin complex. Other optional ingredients well known to the pharmacist's art may also be included in amounts generally known for these ingredients, for example, natural or artificial sweeteners, flavoring agents, colorants and the like to provide a palatable and pleasant looking final product; acidulants, for example, citric acid, ascorbic acid, or malic acid and the like to adjust pH; antioxidants, for example, butylated hydroxy anisole or butylated hydroxy toluene; and preservatives, for example, methyl or propyl paraben or sodium benzoate, to prolong and enhance shelf life.

In preparing the liquid oral dosage forms, the coated drug-resin complexes are incorporated into an aqueous-based orally acceptable pharmaceutical carrier consistent with conventional pharmaceutical practices. An "aqueous-based orally acceptable pharmaceutical carrier" is one wherein the entire or predominant solvent content is water. Typical carriers include simple aqueous solutions, syrups, dispersions and suspensions, and aqueous based emulsions such as the oil-in-water type. Preferably, the carrier is a suspension of the pharmaceutical composition in an aqueous vehicle containing a suitable suspending agent. Suitable suspending agents include Avicel RC-591 (a microcrystalline cellulose/sodium carboxymethyl cellulose mixture available from FMC), guar gum and the like. Such suspending agents are well known to those skilled in the art. While the amount of water in the compositions of this invention can vary over quite a wide range depending upon the total weight and volume of the drug-resin complex and other optional non-active ingredients, the total water content, based on the weight of the final composition, will generally range from about 20 to about 75%, and, preferably, from about 20 to about 40%, by weight/volume.

Although water itself may make up the entire carrier, typical liquid formulations may contain a co-solvent, for example, propylene glycol, glycerin, sorbitol solution and the like, to assist solubilization and incorporation of water-insoluble ingredients, such as flavoring oils and the like, into the composition. In general, therefore, the compositions of this invention preferably contain from about 5 to about 25 volume/volume percent and, most preferably, from about 10 to about 20 volume/volume percent, of the co-solvent.

As used herein, unless otherwise defined, the term "substantially free of organic solvent" means that the composition has less than 5% by weight of organic solvents, preferably, less than 2% by weight of the composition. More preferably, the term "substantially free of organic solvent" means that the composition has less than 1% by weight of organic solvents. Organic solvents include, but are not limited to, chloroform, methylene chloride, acetone, tetrahyrdrofuran, and the like.

Specific Gravity

Any of the methods described herein may include the step of altering the specific gravity of the liquid drug suspension. Methods of altering the specific gravity of a liquid suspension are known in the art. For example, U.S. Publication No. 2009/0176884, which is incorporated by reference herein in its entirety, describes a method of preparing liquid suspensions comprising suspending at least one pharmaceutically active compound in a suspending system (e.g., based on a thixotropic system) and matching/equilibrating the true density of the resin containing at least one pharmaceutical active with the specific gravity of the aqueous medium via a density adjusting agent. Accordingly, any of the methods described herein may further comprise a step of suspending drug-containing resin particles in a suspending system to alter the specific gravity of the liquid drug suspension.

The liquid drug suspension may be manufactured using techniques known in the art such as those described in U.S. Publication No. 2006/0193877, which is hereby incorporated by reference in its entirety. Moreover, as described herein, one of skill in the art may modify the drug suspension to modify a drug release profile and ultimately achieve a desired in vivo serum concentration profile.

Methods for Predicting In Vivo Performance

The invention provides for a method of obtaining in vim) drug release information for a liquid drug suspension which is predictive of in vivo performance. In one embodiment, the method comprises (a) suspending drug-containing resin particles in a liquid suspension preparation; (b) obtaining an in vitro dissolution profile of a test sample obtained from the suspension preparation of (a); and (c) correlating the in vitro dissolution profile of the test suspension to a desired in vivo serum concentration profile observed in a subject who has been administered a finally formulated and fully stabilized (aged) suspension product. The correlation to the desired in vivo profile may well be accomplished by comparison to the in vitro dissolution profile of a fully aged suspension having an IVIVC to the desired in vivo profile. Alternatively, the test suspension profile may be obtained before full aging of the test suspension and the correlation may involve comparing the test suspension profile to a control dissolution profile for the suspension that produced the IVIVC, but obtained for a sample pulled from the suspension at the same delay after production of the suspension but before full aging as the sample of the test suspension was pulled. Typically, the liquid suspension preparation in step (a) will be substantially similar in physicochemical characteristics to a finally formulated and fully aged suspension. The control dissolution profile may also be determined for a suspension substantially similar in physicochemical characteristics to a finally formulated and fully aged suspension.

This invention is particularly adapted to suspensions which, as manufactured, comprise elements that are likely to lead to disequilibrium. For example, the suspension may comprise drugs having different binding affinities or binding constants, or ion-exchange resins having different affinities. In another mode, the suspension may contain both ionically-bound and unbound drug. In yet another mode, the suspension may comprise partially loaded resins, free resins, resin sites without bound drug. In still another mode, the pH of suspension may change over time. In a preferred embodiment, the suspension comprises two different drugs. In a more preferred embodiment, the drugs are chlorpheniramine and hydrocodone.

Sampling for Predictive Assays

One can predict whether the test liquid drug suspension will have an in vivo serum profile like the control by comparing the in vitro dissolution profile for the liquid drug suspension obtained as described above to a control in vitro dissolution profile obtained by performing the same in vitro dissolution assay on a control liquid drug suspension having a desired in vivo serum concentration profile. Typically, the desired in vivo serum concentration profile is one that is observed in a subject who has been administered a finally formulated and fully aged suspension product.

The sample liquid drug suspension may be a suspension as described herein. An aliquot of the sample liquid drug suspension may be tested by introducing it into dissolution medium. The aliquot may be removed from the test suspension at any time after the suspension is prepared. In one mode, the aliquot may be taken after a period necessary for a drug suspension to fully age (i.e., after equilibrium is reached between various forms of a particular drug in the suspension). The aliquot may also be taken after a pre-determined hold period, wherein the pre-determined hold is substantially less than the period necessary for a drug suspension to fully age. Suitable hold periods include four hours after the suspension is completely manufactured, or 16 hours after completion of manufacture, or one, two, four or five days or one to two weeks. In any case, the aliquot of the sample is placed into the dissolution medium as soon as practical after it is removed.

Methods for Obtaining a Dissolution Profile for a Liquid Drug Suspension

When formulating a liquid drug suspension for therapy, it is important to measure in vitro drug release as a function of time (i.e., a dissolution profile) for various reasons such as quality control and generating data to support in vivo bioavailability. The in vitro dissolution assay according to this invention is an assay which produces such a profile. In particular, the in vitro dissolution assay may be an assay described herein or any similar assay known in the art.

This invention provides for methods of obtaining in vitro dissolution profiles for liquid drug suspensions. The in vitro dissolution protocol may be an assay that comprises two or more medium conditions, beginning with an acidic pH (e.g., less than pH 2.0) for a certain period of time and which is subsequently raised to an acid-to-neutral pH (e.g., above pH 6.0). Alternatively, the in vitro dissolution may be an assay that comprises an acidic pH (e.g., simulated gastric fluid) for a certain period of time.

In one embodiment, the method comprises (a) introducing an aliquot of a sample liquid drug suspension into a dissolution medium which initially has a pH less than 2.0; (b) adjusting the pH to above 6.0, preferably above 6.5, and more preferably about 6.8 about 2 hours after initiation of the assay; and (c) producing an in vitro dissolution profile for the liquid drug suspension by determining the concentration of drug in the dissolution medium at a series of time points after the introduction of the drug containing aliquot into the dissolution medium. In a particular embodiment, the method comprises (a) introducing an aliquot of a sample liquid drug suspension into a dissolution medium which initially has a pH less than 2.0; (b) adjusting the pH to between 5.6 and 6.3 about 1 hour after initiation of the assay; (c) adjusting the pH to above 6.5, preferably about 6.8 about 2 hours after initiation of the assay; and (d) producing an in vitro dissolution profile for the liquid drug suspension by determining the concentration of drug in the dissolution medium at a series of time points after the introduction of the drug into the dissolution medium.

In another embodiment, the method comprises
(a) introducing an aliquot of a sample liquid drug suspension into a dissolution medium, where the dissolution medium contains about 900 mL of 0.1 N HCl;
(b) adding a buffered basic solution equal to about $\frac{1}{10}$ the volume of the dissolution medium about one hour after the introduction to bring the pH to between 5.6 and 6.3;
(c) adding a buffered basic solution equal to about 1-10% of the volume of the dissolution medium after about two hours from the introduction to bring to pH above 6.5;
(d) producing an in vitro dissolution profile for the liquid drug suspension by determining the concentration of drug in the dissolution medium at a series of time points after the introduction of the aliquot into the dissolution medium.

In another embodiment, the method comprises introducing an aliquot of a sample liquid drug suspension into a dissolution medium which mimics gastric fluid comprising 0.1N HCl with 0.3% (w/v) sodium dodecyl sulfate (also known as sodium lauryl sulfate). In a particular embodiment, this dissolution assay is performed using a liquid drug suspension comprising chlorpheniramine. In another embodiment, the method comprises introducing an aliquot of a sample liquid drug suspension into a dissolution medium comprising simulated gastric fluid TS with 0.20% (w/v) sodium dodecyl sulfate (also known as sodium lauryl sulfate). In a particular embodiment, this dissolution assay is performed using a liquid drug suspension comprising hydrocodone.

Various methods of adjusting pH are known in the art and may be used herein. For example, the pH may be modified by steps which involve adding pre-determined amounts of particular reagents (e.g., a potassium phosphate/sodium hydroxide solution) at set times. (See also U.S. Pat. No. 5,980,882, which is incorporated by reference herein in its entirety). The invention contemplates that for any of the methods of obtaining a dissolution profile described herein, these methods may be performed using a USP Type II (paddle) apparatus and agitating the solution at 100 rpm. The sample may preferably be agitated at 100 rpm in view of the high viscosity of liquid drug suspensions. The inventors determined that typical paddle speeds of 25/75 rpm may not disperse suspension matrices that accumulated at the base of the dissolution vessel. This could cause a "cone effect" that essentially keeps the coated resin particles from being distributed throughout the vessel and initiating their release characteristics, at least early in the dissolution time course. (Contrast FDA website on the world wide web at accessdata.fda.gov/scripts/cder/dissolution/dsp_SearchResults_Dissolutions.cfm, for protocol of dextromethorphan polistirex.)

Methods of Obtaining an In Vitro/In Vivo Correlation

These methods may also include the steps of producing an in vitro dissolution profile of the liquid drug suspension and comparing this in vitro dissolution profile to a control in vitro dissolution profile obtained by performing an in vitro dissolution assay on a control liquid drug suspension as described herein. The dissolution profile may be obtained by determining the concentration of drug in any of the dissolution media described herein.

The inventors have discovered that an in vitro dissolution profile obtained using a GI model provides better correlation to in vivo release than simulated gastric fluid alone. In a preferred embodiment, the dissolution profile has a "Level A correlation." This is a point-to-point correlation that directly relates to the in vitro and in vivo data. Level A models compare the fraction of the drug absorbed in the body, as is measured by plasma data, directly to the rate of dissolution in an in vivo setting. The percent of drug absorbed is calculated by model dependent techniques such as the Wagner-Nelson procedure or Loo-Riegelman method or by independent numerical deconvolution. The relationship is usually linear, although that is not always the case, as described herein with coated Hydrocodone (HCB) Polistirex (See. Example 3 below), and can serve as an alternative to in vivo studies. Nonetheless, due to the strong mathematical relationship between the in vitro and in vivo data in Level A correlation studies, minor changes in the formulation, method of manufacture, and even amount of active can be adjusted without the need for further human clinical trials. The in vitro dissolution profile obtained in this method, and the methods described herein may be predictive of bioequivalence.

Methods of Preparing Suspensions with Desired Release Profiles

The invention also provides for a method of formulating liquid drug suspensions. In one embodiment, the invention provides for a method of formulating a liquid drug suspension comprising suspending drug-contain resin particles in a liquid suspension, wherein the drug-containing resin particles comprise a first plurality of particles comprising a water-permeable coating and a second plurality of uncoated particles, and wherein the first and second plurality of particles contain the same drug.

Methods for Qualifying Drug-Containing Resin Particles

In order to formulate a liquid drug suspension using drug-containing resin particles, it is necessary to confirm that the particles are suitable for its intended use. Indeed, the initial particles are tested to confirm that the particles meet a specified criteria and thus will ensure reproducibility of the final suspension from batch to batch. The invention provides for methods of qualifying drug-containing resin particles. These methods permit the inspection of incoming materials, facilitate the correction of in-process errors, and reduce costs of manufacturing.

In one embodiment, the invention provides a method for confirming the acceptability of a quantity of drug-containing resin particles to be formulated into a suspension product without waiting for the final product batch to be formulated and fully aged. In a preferred embodiment, this method comprises (a) suspending a quantity of drug-containing resin particles to provide a test suspension, wherein the test suspension is substantially similar in physicochemical characteristics to a final drug suspension product;

(b) introducing an aliquot of the test suspension into a dissolution medium after a pre-determined hold period from the end of the suspending step, the pre-determined hold period being substantially less than a period necessary for a drug suspension to fully age;

(c) producing a test suspension in vitro dissolution profile by determining the concentration of drug in the dissolution medium at a series of time points after the introduction of the aliquot;

(d) comparing said test suspension in vitro dissolution profile to a control in vitro dissolution profile obtained by performing an in vitro dissolution assay on a control liquid drug suspension, wherein the control in film dissolution assay is performed after the same pre-determined hold period, which is substantially less than the period necessary for a drug suspension to fully age; and (e) accepting or rejecting said quantity of drug-containing resin particles based on the comparison in step (d). A suitable control liquid drug suspension would be one having a desired in vivo serum concentration profile observed in a subject who has been administered a finally formulated and fully aged suspension product.

These methods may also include the steps of producing an in vitro dissolution profile of the liquid drug suspension and comparing this in nitro dissolution profile to a control in vitro dissolution profile obtained by performing an in vitro dissolution assay on a control liquid drug suspension as described herein. The dissolution profile may be obtained by determining the concentration of drug in any of the dissolution media described herein.

The invention provides that the drug-containing resin particles are accepted if the test suspension in vitro dissolution profile is equivalent to the control in vitro dissolution profile. If the particles do not meet the specified criteria, then the particles may be modified as described herein.

The pre-determined hold period may be any time period so long as the pre-determined hold period is substantially less than a period necessary for a drug suspension to fully age. For example, the pre-determined hold period may be any period long enough after completion of the suspension of the drug-containing resin particles to permit reproducible sampling of the drug suspension from batch-to-batch, such as 10 minutes, but preferably at least 4 hours, optionally at least 20, 24, or 48 hours, or a similar period which can be shown to produce an in vitro dissolution profile which is predictably consistent with the profile of the fully aged suspension product. Also, the pre-determined hold period must be constant from liquid suspension to liquid suspension (i.e., batch to batch) to ensure reproducibility.

The dissolution medium may comprise any of the dissolution media described herein. For example, the dissolution medium may initially have a pH less than 2.0, and then be adjusted to have a pH above 6.0, preferably above 6.5, and more preferably about 6.8 after about 2 hours.

In a typical embodiment, the test suspension has a composition substantially equivalent in physico-chemical characteristics to an intended final formulation. The test suspension may have the same ingredients as a final drug suspension. Preferably, the test suspension has the same ingredients as a final drug suspension except that the test suspension may not contain coloring agents, flavoring agents, preservatives, non-ionic suspending agents, surfactants, or combinations thereof.

The quantity of drug-containing resin particles may comprise a first plurality of particles comprising a first drug and a second plurality of particles comprising a second drug. The first plurality of particles may further comprise a water-permeable coating, and the second plurality of particles may omit the water-permeable coating (i.e., the particle is uncoated). Alternatively, the first and second plurality of particles may comprise the same drug as described herein.

The coating may be any coating described herein. A preferred coating is ethylcellulose.

The first and second drugs may be any of the drugs described herein that one of skill in the art would combine for a therapeutic treatment (i.e., a treatment comprising the combination of two different drugs). In a preferred embodiment, the first drug is hydrocodone and the second drug is chlorpheniramine.

It is understood that the various aspects described in this and other sections may be combined. For example, the invention contemplates a method for confirming the acceptability of quantity of drug-containing resin particles, where the drug-containing resin particles comprise a first plurality of particles comprising hydrocodone and an ethylcellulose coating, and a second plurality of uncoated particles comprising a chlorpheniramine.

Methods of Preparing Suspensions with Desired Release Profiles

The invention also provides for a method of formulating liquid drug suspensions. In one embodiment, the invention provides for a method of formulating a liquid drug suspension comprising suspending drug-contain resin particles in a liquid suspension, wherein the drug-containing resin particles comprise a first plurality of particles comprising a water-permeable coating and a second plurality of uncoated particles, and wherein the first and second plurality of particles contain the same drug. In a preferred embodiment, the liquid drug suspension provides an early onset of therapeutic value, while masking the taste of the drug and maintaining bioequivalence and bioavailability.

The invention may provide an early onset of therapeutic value in which at least 15% more of the drug will be released within the first 15, 30, 60, 75, or 90 minutes of administration, as compared to conventional forms of the same drug. Preferably substantially all of the early release of drug will occur in the gastric space, with only an insignificant amount of drug released in the oral cavity, in order to mask the taste of the drug.

The coating may be any coating described herein. A preferred coating is ethylcellulose. The drug may be any of the drugs described herein.

It is understood that the various aspects described in this and other sections may be combined.

Methods of Designing a Liquid Drug Suspension Formulation by Refining Drug-Containing Resin Particles In order to formulate a liquid drug suspension using drug-containing resin particles, it may be necessary to modify the particles to ensure that the drug suspension is equivalent to a desired profile. As such, the invention provides for methods of designing liquid drug suspensions by refining drug-containing resin particles.

In one embodiment, the invention provides for a method for designing a liquid dosage form comprising (a) obtaining an initial preparation of drug-containing resin particles;

(b) combining a pre-determined amount of these initial drug-containing resin particles with a plurality of excipients in a container to form an initial liquid drug suspension;

(c) introducing an aliquot of said initial drug suspension into a dissolution medium after a pre-determined hold period, wherein said pre-determined hold is substantially less than a period necessary for a drug suspension to fully age; and (d) producing a test suspension in vitro dissolution profile by determining the concentration of drug in the dissolution medium at a series of time points after the introduction of the test suspension, (e) comparing said test suspension in vitro dissolution profile to a control in vita dissolution profile obtained by performing an in vitro dissolution assay on a control liquid drug suspension, where the control in vitro dissolution assay is performed after the same pre-determined hold period. A suitable control liquid drug suspension would be one having a desired in vivo serum concentration profile observed in a subject who has been administered a finally formulated and fully aged suspension product.

If the test suspension in vitro dissolution profile is not equivalent to the control in vivo dissolution profile, then a new batch of drug-containing resin particles is prepared using a process modified as described below, and the modified drug-containing resin particles are combined with the plurality of excipients of step (b) to form a modified liquid drug suspension; and steps (c)-(e) are repeated until the in vitro dissolution profile of said modified liquid drug suspension does match the control in vitro dissolution profile.

Particle Size and Distribution

The method may comprise the step of modifying the particle size and/or size distribution. It is beneficial to have a homogenous mixture of particles (i.e., less variance in particle size and a tighter distribution of particle sizes) to maintain uniformity in a liquid drug suspension. This may be achieved by passing the particles through a screen or a series of screens, or by air classification or other fluid classification. Large particles may contribute to a "gritty" mouthfeel, so it is preferred to have 80% or more of the particles below 200 μm in diameter. Smaller particles tend to provide a smoother product, but it may be difficult to achieve small particle size without milling the particles.

Coating Weight

The step of modifying may comprise increasing or decreasing the amount of the coating. For example, the step of modifying may comprise increasing the weight of the coating to decrease the rate of dissolution of the test suspension. Alternatively, the step of modifying may comprise decreasing the weight of the coating to increase the rate of dissolution of the test suspension.

Methods of increasing or decreasing the amount of the coating are known in the art. See, e.g., U.S. Pat. Nos. 4,221, 778 and 4,996,047; U.S. Publication Nos. 2006/0193877; 2007/0059270; 2007/01400983; and 2007/0148239. The disclosure of each of these patents and publications is incorporated by reference herein in their entireties.

Drug Loading

The method may comprise modifying the amount of drug loaded onto the particles. For example, the step of modifying may comprise increasing the amount of drug loaded above the holding capacity of the drug-containing resin particle to increase the rate of dissolution of the test suspension. (See U.S. Publication Nos. 2007/0059270; 2007/01400983; and 2007/0148239). Alternatively, the step of modifying may comprise decreasing the amount of drug loaded below holding capacity on said drug-containing resin particle to decrease the rate of dissolution of the test suspension.

Methods of modifying drug loading are known in the art. See, e.g., U.S. Pat. Nos. 4,221,778 and 4,996,047; U.S. Publication Nos. 2006/0193877; 2007/0059270; 2007/01400983; and 2007/0148239. The disclosure of each of these patents and publications is incorporated by reference herein in their entireties.

It is understood that the various aspects described in this and other sections may be combined (e.g., the methods may use any of the dissolution media described herein, the drug-containing resin particles may comprise a first plurality of particles comprising a first drug and a second plurality of particles comprising a second drug, etc.)

Methods of Formulating a Liquid Drug Suspension by Refining Suspension Parameters In order to formulate a liquid drug suspension, it may be necessary to modify the drug suspension to ensure that it is equivalent to a desired profile. As such, the invention provides for methods of formulating liquid drug suspensions by refining the composition of the liquid drug suspension and/or the procedure for its preparation.

In one embodiment, the invention provides for a method for formulating a liquid dosage form comprising (a) obtaining drug-containing resin particles;

(b) combining a pre-determined amount of said drug-containing resin particles with a plurality of excipients in a container to form an initial liquid drug suspension;

(c) introducing an aliquot of said initial drug suspension into a dissolution medium after a pre-determined hold period, wherein said pre-determined hold is substantially less than a period necessary for a drug suspension to fully age;

(d) producing a test suspension in vitro dissolution profile by determining the concentration of drug in the dissolution medium at a series of time points after said introduction; and (e) comparing said test suspension in vitro dissolution profile to a control in vitro dissolution profile obtained by performing an in vivo dissolution assay on a control liquid drug suspension, wherein said control in vitro dissolution assay is performed after a pre-determined hold period. A suitable control liquid drug suspension is one having a desired in vivo serum concentration profile observed in a subject who has been administered a finally formulated and fully aged suspension product.

If the test suspension in vitro dissolution profile is not equivalent to the control in vivo dissolution profile, then a modified suspension is prepared using a process described below; and steps (c)-(e) are repeated until the in vitro dissolution profile of said modified liquid drug suspension is equivalent to the control in vitro dissolution profile.

Ionic Salts

The method may comprise modifying the ionic strength or concentration of the initial liquid drug suspension. For example, the step of modifying may comprise increasing the ionic strength or concentration of the initial liquid drug suspension which has been found to increase the rate of dissolution of the test suspension. Alternatively, the step of modifying may comprise decreasing the ionic strength or concentration of the initial liquid drug suspension which has been found to decrease the rate of dissolution of the test suspension.

Methods of modifying ionic strength or concentration are disclosed in U.S. Publication No. 2009/0011027. The disclosure of this publication is hereby incorporated by reference in its entirety.

Active Resin-Site Balance

The method may comprise modifying the active resin-site balance of the initial liquid drug suspension. For example, the step of modifying may comprise changing the active resin-site balance to increase or decrease the rate of dissolution of the test suspension. The rate of dissolution may be decreased by adding a pre-determined amount coated free resin to the container (i.e., a coated particle that does not contain any drug). The rate of dissolution may also be decreased by adding a pre-determined amount uncoated free resin to the container (i.e., an uncoated particle that does not contain any drug).

Alternatively, the rate of dissolution may be increased by adding a pre-determined amount of free drug to the container.

It is understood that the various aspects described in this and other sections may be combined (e.g., the methods may use any of the dissolution media described herein, the drug-containing resin particles may comprise a first plurality of particles comprising a first drug and a second plurality of particles comprising a second drug, etc.)

Suspensions and Methods of Preparing Suspensions Bioequivalent to a Target Product The invention provides for methods of making liquid drug suspensions that are bioequivalent to a target product. In some embodiments, various parameters described herein may be adjusted such that the in vitro dissolution profile is equivalent to a desired profile of a target product. In a preferred embodiment, the invention provides for a method of making a liquid drug suspension that is bioequivalent to Tussionex® drug suspension using the methods described herein.

The invention also provides for extended release liquid drug suspensions that are bioequivalent to a target product. In one embodiment, the invention provides a pharmaceutical composition comprising (a) hydrocodone adsorbed on ion-exchange polystirex to form coated drug-resin particles; (b) chlorpheniramine adsorbed on ion-exchange polystirex to form uncoated drug-resin particles; and (c) at least one liquid carrier, where at least 50% the coated drug-resin particles are larger than 50 μm. Preferably, at least 80% of the coated drug-resin particles in this embodiment are smaller than 200 μm. In a preferred embodiment, the invention provides for an extended release liquid drug suspension comprising hydrocodone polystirex and chlorpheniramine polystirex that is bioequivalent to Tussionex® drug suspension.

The following examples describe various methods of obtaining dissolution profiles including a method of making a liquid drug suspension that is bioequivalent to Tussionex® drug suspension. These examples are not intended to limit the invention in any way.

Example 1

Dissolution Profile of Chlorpheniramine Polistirex Drug Substance

The dissolution profiles of hydrocodone polistirex and chlorpheniramine polistirex are considered. Hydrocodone polistirex resinate was prepared as described in U.S. Pub. Nos. 2007/0140983, 2007/0059270, and/or 2007/0148239. Chlorpheniramine maleate is bound to polistirex cation exchange resin. The resin was polistirex IRP-69 from Rohm & Haas for both drugs. A suspension containing both of these resinates in suspension was manufactured using the formula detailed in Table 1 and the process detailed in Table 2.

TABLE 1

Test Formula

| Ingredient | Application | Ingredient Percent |
|---|---|---|
| Purified Water, USP | Hydration Agent | 30.8% |
| Ascorbic Acid | pH Adjuster | 0.03% |
| Propylene Glycol, USP | Solvent | 3.33% |
| Methylparaben | Preservative | 0.13% |
| Propylparaben | Preservative | 0.04% |
| Polysorbate 80 | Surfactant | 0.08% |
| Xanthan Gum | Thickener | 0.5% |
| Vegetable Oil | Viscosity Agent | 0.17% |
| Liquid Orange Color | Colorant | 0.002% |
| D&C Yellow # 10 | Colorant | 0.002% |
| Natural Mango Flavor | Flavor | 0.03% |
| Uncoated Chlorpheniramine Polistirex Resin | Active | 0.59% |
| Coated Hydrocodone Polistirex Resin | Active | 1.0% |
| Sucrose | Sweetener | 12.5% |
| High Fructose Corn Syrup | Sweetener & Viscosity Agent | 37.5% |
| Purified Water, USP | Diluent | ≈13.2% |

TABLE 2

Manufacturing Instructions

| Step Number | Basic Manufacturing Instructions |
|---|---|
| 1 | Mix the Purified Water and Ascorbic Acid in the main container. |
| 2 | Heat Propylene Glycol to ≈50° C. - add the Parabens, Polysorbate 80, and Xanthan Gum. |
| 3 | Add the Xanthan Gum/Paraben solution to the main container and hydrate for 4 to 4.5 hours. |
| 5 | Add the Vegetable Oil, Colors, and Flavor to the main container. |
| 6 | Sprinkle Chlorpheniramine and Hydrocodone Resin into the main container. |
| 7 | Add Sucrose to the main container. |
| 8 | Add Corn Syrup to the main container. |
| 9 | QS with Water. |

Figure 4:
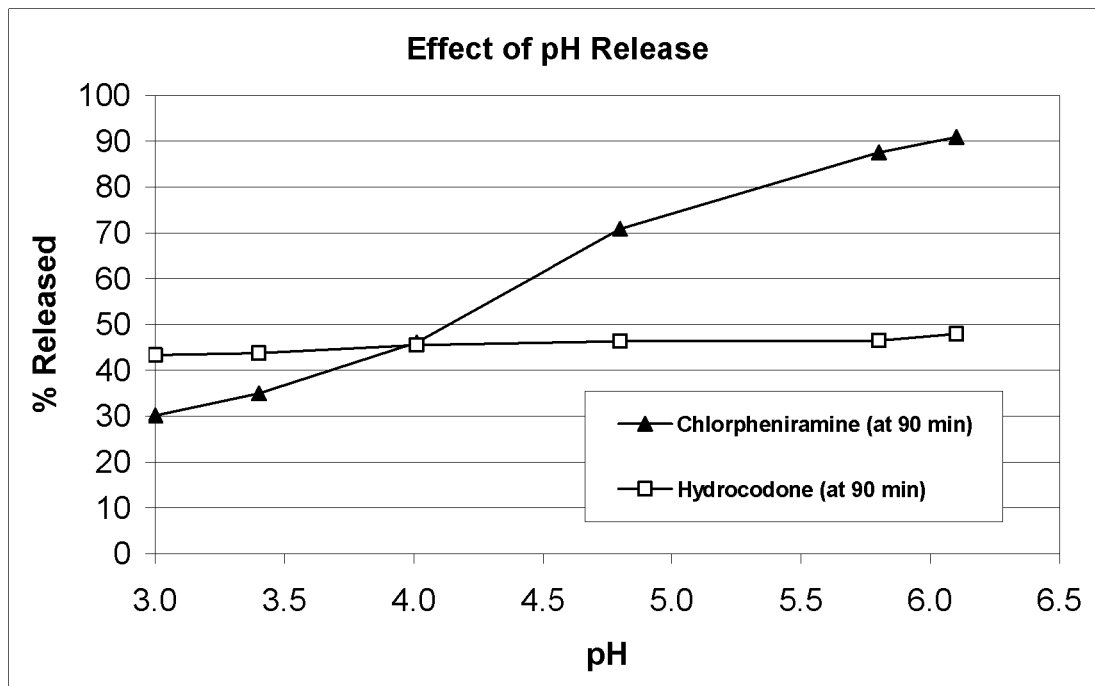
FIG. 4 shows the amount of drug from chlorpheniramine polistirex and hydrocodone polistirex released in vitro after 90 minutes in various pH buffers.
Figure 5:
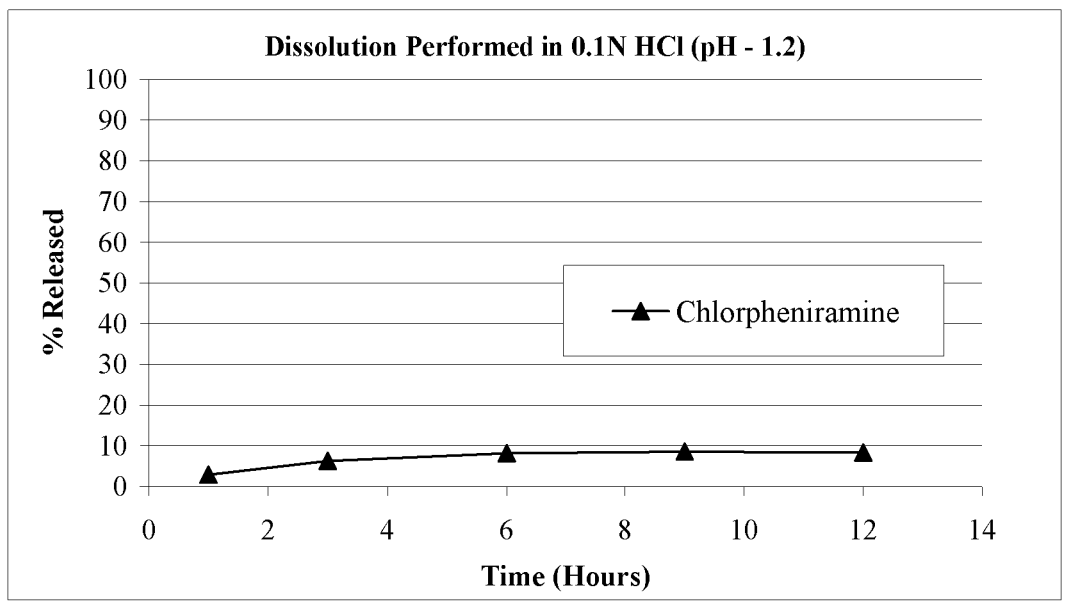
FIG. 5 shows an in vitro dissolution profile of chlorpheniramine polistirex in 0.1 N HCl over time.

Dissolution testing was performed on samples of the suspension prepared using the protocol described above and stored for about 18 months. Samples of the suspension were pulled after mixing for 30 minutes and tested in USP Type 11 apparatus for dissolution testing (See FIGS. 4 and 5). The apparatus contained 900 ml of 0.1N HCl, and pH was adjusted by adding various amounts of Potassium Phosphate Solution containing 0.5M Potassium Phosphate Monobasic and 1.2M Sodium Hydroxide.

To achieve a pH of 3.00, 72.6 mL of the Potassium Phosphate Solution was added.

To achieve a pH of 3.40, 75.7 mL of the Potassium Phosphate Solution was added.

To achieve a pH of 4.01, 77.0 mL of the Potassium Phosphate Solution was added.

To achieve a pH of 4.80, 77.8 mL of the Potassium Phosphate Solution was added.

To achieve a pH of 5.80, 80.9 mL of the Potassium Phosphate Solution was added.

To achieve a pH of 6.10, 82.9 mL of the Potassium Phosphate Solution was added.

These amounts were added to 900 ml of 0.1N HCl, and samples were pulled for drug assay 90 minutes after the suspension was added.

These experimental results demonstrate that release of chlorpheniramine from polistirex resin is dependent upon the pH of the environment, while release of hydrocodone is essentially pH-independent.

The chlorpheniramine polistirex drug substance does not include any sustained release coating system, yet it is still considered modified release. The mechanism of the drug release is purely pH and ion dependent in practice. The extended release characteristics of the drug are created by the inability of the drug to become unbound from the polistirex resin in an acidic environment (the stomach), while releasing in the higher pH environment of the gastrointestinal tract.

Figure 6:
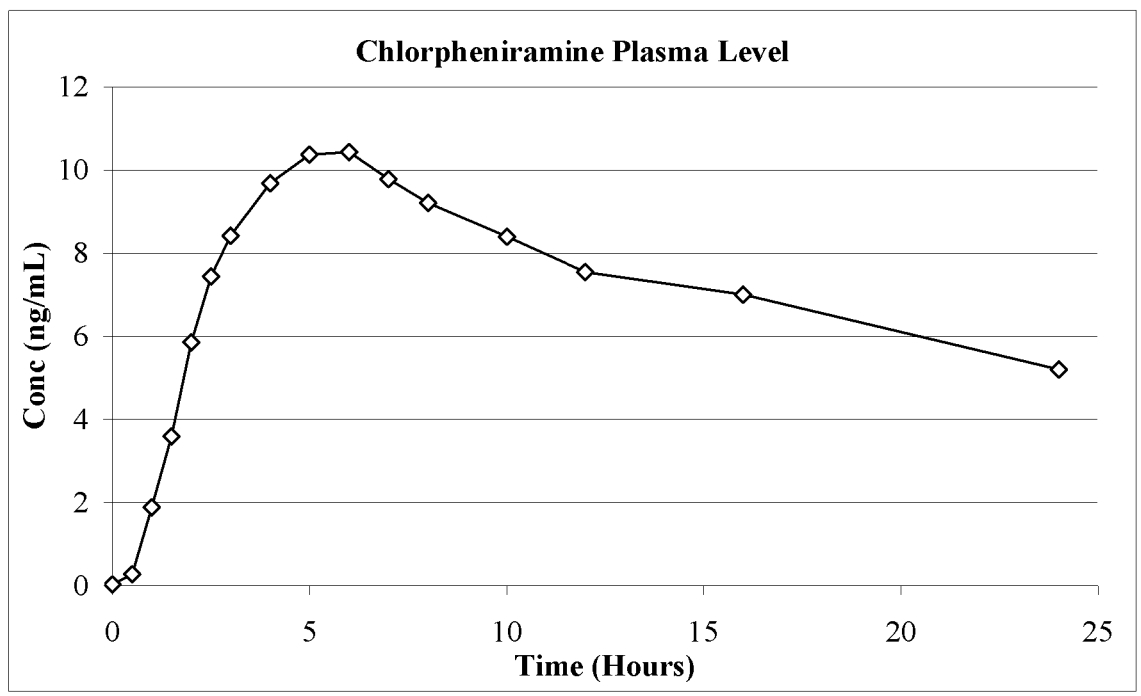
FIG. 6 shows an in vivo serum concentration profile of chlorpheniramine polistirex.

Chlorpheniramine also has a long biological half life in the body, between 12 and 43 hours in adults and 10 to 13 hours in children (see Physician's Assistant's Drug Handbook, $2^{nd}$ Edition; Springhouse Publishing 2001), which aids in extending the effect of the antihistamine. The in-vivo data, depicted in FIG. 6, demonstrated the extended release nature of a suspension containing an uncoated chlorpheniramine polistirex drug substance.

Example 2

Effect of Coating Level on Release Profile for Hydrocodone Polistirex

Batches of ethylcellulose coated hydrocodone polistirex resinate were prepared using three coating application iterations. Hydrocodone polistirex resinate was prepared as described in U.S. Pub. Nos. 2007/0140983, 2007/0059270, and/or 2007/0148239. The initial coating application was stopped when the coating level reached an initial low coating level (weight per weight basis), the second coating application added an additional coating to an intermediate coating level (medium), and the final application added an additional coating for a final coating level (high).

Figure 7:
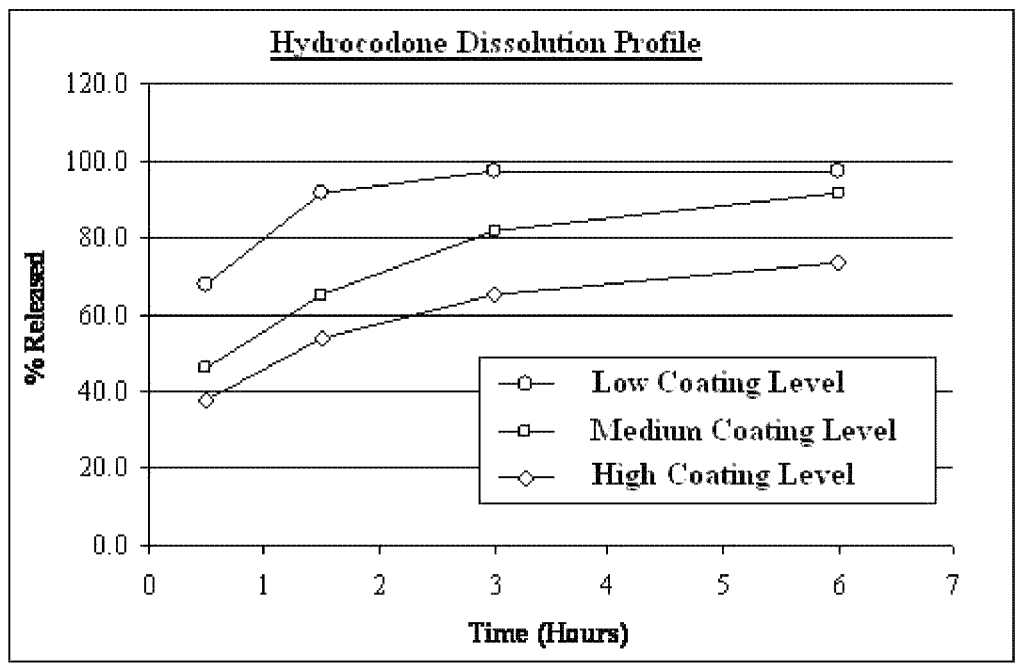
FIG. 7 shows in vitro dissolution profiles for three batches of ethylcellulose coated hydrocodone polistirex resinates using different coating levels (low, medium, and high).

Separate suspensions of the coated hydrocodone resinates at each coating level were prepared according to the protocol of Example 1. Samples of each suspension were pulled after two months in storage and tested in USP Type II apparatus for dissolution testing. The dissolution media initially contained 900 mL of 0.1N HCl (i.e., pH of 1.2) for the first hour. After the first hour, approximately 85 mL of potassium phosphate/ sodium hydroxide buffer was added to bring the pH up to ~4.5, then after the second hour the pH is was finally brought up to ~6.8 by adding approximately 15 mL of potassium phosphate/sodium hydroxide buffer. The potassium phosphate/sodium hydroxide buffer is 0.5M potassium phosphate monobasic and 1.2M NaOH. The concentration at the first buffer addition is 0.04M potassium phosphate monobasic and 0.10M NaOH. The concentration at the final concentration is 0.05M potassium phosphate monobasic and 0.12M NaOH. The sample was agitated at a 100 rpm. The results of all three dissolution tests are presented in FIG. 7.

These results demonstrate the ability to significantly alter the release profile of the coated hydrocodone resinate through additional coating iterations, thereby exhibiting the primary release control mechanism. Using this coating iteration process, each batch of hydrocodone resinate can be manufactured to the appropriate release level. Once the final coating has been completed, the finished coated hydrocodone resinate can be tested for quality control and released for manufacturing of final suspension products.

The inventors concluded that the required coating level of coated hydrocodone polistirex resin may vary slightly from batch to batch in order to meet the required release specifications. This coating level adjustment strategy, which will compensate for any slight differences in the material or process used to manufacture the coated hydrocodone polistirex resin, will produce a coated hydrocodone polistirex resin that will consistently deliver a desired dissolution release profile.

Example 3

Dissolution Protocol Leading to In Vitro/In Vivo Correlation

Figure 8:
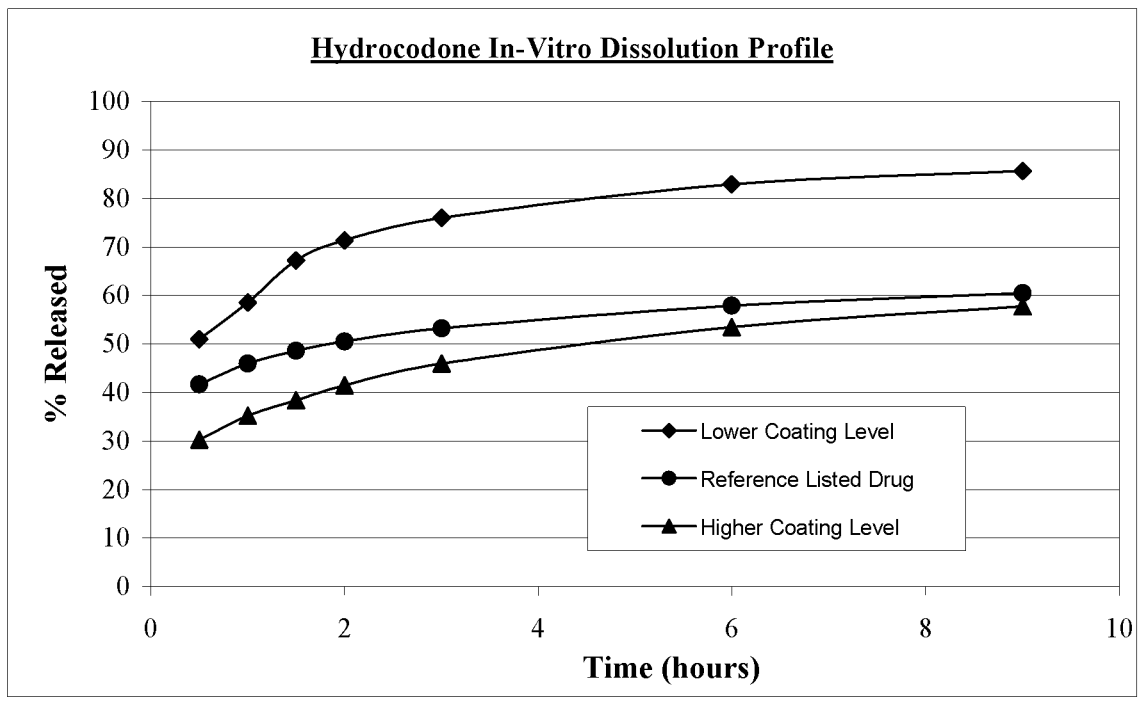
FIG. 8 shows in vitro dissolution profiles for hydrocodone coating levels that bracket Tussionex®.

A. Dissolution Results of Low Coating Level Hydrocodone Polistirex, High Coating Level Hydrocodone Polistirex, and Tussionex® Pennkinetic® ER Suspension Hydrocodone Polistirex with the Proposed Dissolution Procedure Hydrocodone coating levels that bracket the Reference Listed Drug (i.e., Tussionex®) were determined by the results of in-vitro dissolution testing (as demonstrated in FIG. 8, which was a pilot batch). Suspensions utilizing hydrocodone resinate with a lower coating level and a higher coating level were selected.

Tussionex® antitussive-antihistamine suspension contains hydrocodone polistirex (sulfonated styrene-divinyl benzene copolymer) equivalent to 10 mg hydrocodone bitartrate and chlorpheniramine polistirex equivalent to 8 mg chlorpheniramine maleate. To prepare a suspension that is bioequivalent, batches were manufactured using the formula detailed in Table 1 and the process detailed in Table 2 below and hydrocodone polistirex and chlorpheniramine polistirex prepared as described in Examples 1 and 2. Two 100 Liter batches of the drug product were manufactured: (i) Lot A using low coating level hydrocodone polistirex resin; and (ii) Lot B using high coating level hydrocodone polistirex resin.

TABLE 1

Test Formula

| Ingredient | Application | Ingredient Percent |
|---|---|---|
| Purified Water, USP | Hydration Agent | 30.8% |
| Ascorbic Acid | pH Adjuster | 0.03% |
| Propylene Glycol, USP | Solvent | 3.33% |
| Methylparaben | Preservative | 0.13% |
| Propylparaben | Preservative | 0.04% |
| Polysorbate 80 | Surfactant | 0.08% |
| Xanthan Gum | Thickener | 0.5% |
| Vegetable Oil | Viscosity Agent | 0.17% |
| Liquid Orange Color | Colorant | 0.002% |
| D&C Yellow # 10 | Colorant | 0.002% |
| Natural Mango Flavor | Flavor | 0.03% |
| Uncoated Chlorpheniramine Polistirex Resin | Active | 0.59% |
| Coated Hydrocodone Polistirex Resin (Lot A) or (Lot B) | Active | ≈1.0% |
| Sucrose | Sweetener | 12.5% |
| High Fructose Corn Syrup | Sweetener & Viscosity Agent | 37.5% |
| Purified Water, USP | Diluent | ≈13.2% |

TABLE 2

Manufacturing Instructions

| Step Number | Basic Manufacturing Instructions |
|---|---|
| 1 | Mix the Purified Water and Ascorbic Acid in the main container. |
| 2 | Heat Propylene Glycol to ≈50° C. - add the Parabens, Polysorbate 80, and Xanthan Gum. |
| 3 | Add the Xanthan Gum/Paraben solution to the main container and hydrate for 4 to 4.5 hours. |
| 5 | Add the Vegetable Oil, Colors, and Flavor to the main container. |
| 6 | Sprinkle Chlorpheniramine and Hydrocodone Resin into the main container. |
| 7 | Add Sucrose to the main container. |
| 8 | Add Corn Syrup to the main container. |
| 9 | QS with Water. |

Dissolution testing was performed on these two batches using the protocol described below and compared to Tussionex® drug suspension.

The dissolution methodology described herein is based on creating a robust in vitro dissolution test that will correlate with in vivo studies. For oral suspension formulations that contain coated ion-exchange resins suspended in a viscous liquid, dissolution parameters were chosen as follows.

A known quantity of drug-containing liquid suspension is placed in dissolution media which initially contains 900 mL of 0.1N HCl (i.e., pH of 1.2) for the first hour. After the first hour, approximately 85 mL of 0.5M monobasic potassium phosphate and 1.2M NaOH is added to bring the pH up to 5.6 to 6.3, then after the second hour the pH is finally brought up to ~6.8 by adding approximately 15 mL of the potassium phosphate/sodium hydroxide buffer. The dissolution procedure involves apparatus II (paddles) agitating the sample at a 100 rpm.

Dissolutions are run at a fairly high rpm (75-100) due the viscosity of the suspension. The suspension dissolution profile was created by mimicking three pH parameters that are based upon ingestion pH ranges, and listed in Center for Drug Evaluation and Research (CDER) guidance as acceptable for multimedia dissolution tests. (See "Dissolution Testing of Immediate Release Solid Oral Dosage Forms—Appendix A" FDA, CDER, August 1997.)

The potassium salt is added to aid in the buffering of the solution at a constant pH level and to supply cations to the media. These cations have been postulated to exchange with the bound drug and thereby causing a change in the dissolution profile, as compared to deionized water. (See U.S. Pat. No. 4,762,709, which is incorporated by reference herein in its entirety.)

2 mL portions are periodically taken from the medium (e.g., 30 minutes, 1.5 hours and 3 hours, and optionally also 6, 8, and/or 12 hours). The samples are then filtered and analyzed with HPLC to find the percent drug component released from the resinate into the surrounding medium.

Figure 9:
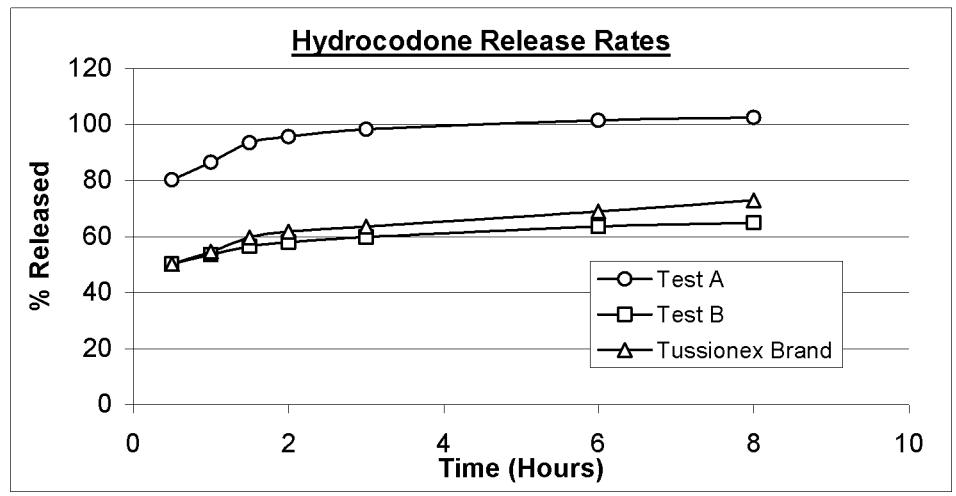
FIG. 9 shows in vitro dissolution profiles for two batches of drug product comprising coated hydrocodone polistirex resins compared to an in vitro dissolution profile for a Tussionex® drug suspension.
Figure 10:
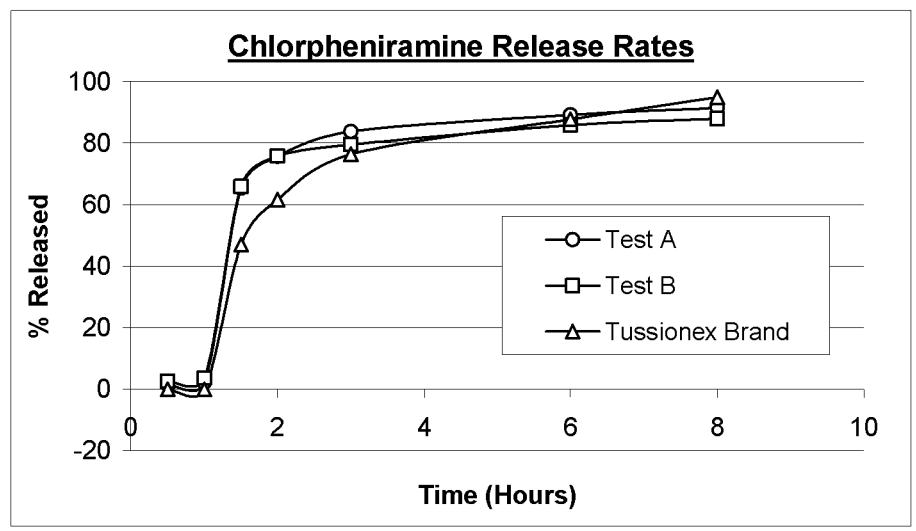
FIG. 10 shows in vitro dissolution profiles for two batches of drug product comprising uncoated chlorpheniramine polistirex resins compared to an in vitro dissolution profile for a Tussionex® drug suspension.

The results of the dissolution assay are shown in FIGS. 9 and 10.

The coating level of the hydrocodone polistirex has an apparent effect on delaying the release of the drug through the semi-permeable membrane, which is evident by the faster release of the low coating level, as compared to the high coating level. The Tussionex® release profile is similar to the high level initially, but is slower to release over time. This profile could also be approximated by a combination of both resins in varying amounts.

The chlorpheniramine polistirex release profiles are only pH dependent, as there is no coating on the resin, therefore these would be statistically similar. After the three hour time point, when the pH adjustment has fully completed, the percent Relative Standard Deviation (% RSD) is less than 5%; after 6 hours all remaining time points the % RSD is less than 3%. This limit is within the method validation protocols for spiked dissolution samples, therefore the release profile of chlorpheniramine in an in vitro situation of lots A and B is equivalent to Tussionex® drug suspension. Lots A and B provided an early onset of therapeutic value.

B. Clinical Results of Low Coating Level Hydrocodone Polistirex, High Coating Level Hydrocodone Polistirex, and Tussionex® Pennkinetic® ER Suspension A randomized three-way crossover, single-dose, open-label pilot study to determine bioavailability of the low coating level hydrocodone polistirex, high coating level hydrocodone polistirex, and Tussionex® drug suspension was conducted with twelve patients and followed the testing and administration procedures of the relevant FDA guidances. (See "Bioavailability and Bioequivalence Studies for Orally Administered Drug Products—General Considerations". FDA, Center for Drug Evaluation and Research (CDER); July, 2002; United States Pharmacopoeia. <1090> Statistical Procedures for Bioequivalence Studies Using a Standard Two-Treatment Crossover Design, USP 30$^{th}$ Edition).

Figure 11:
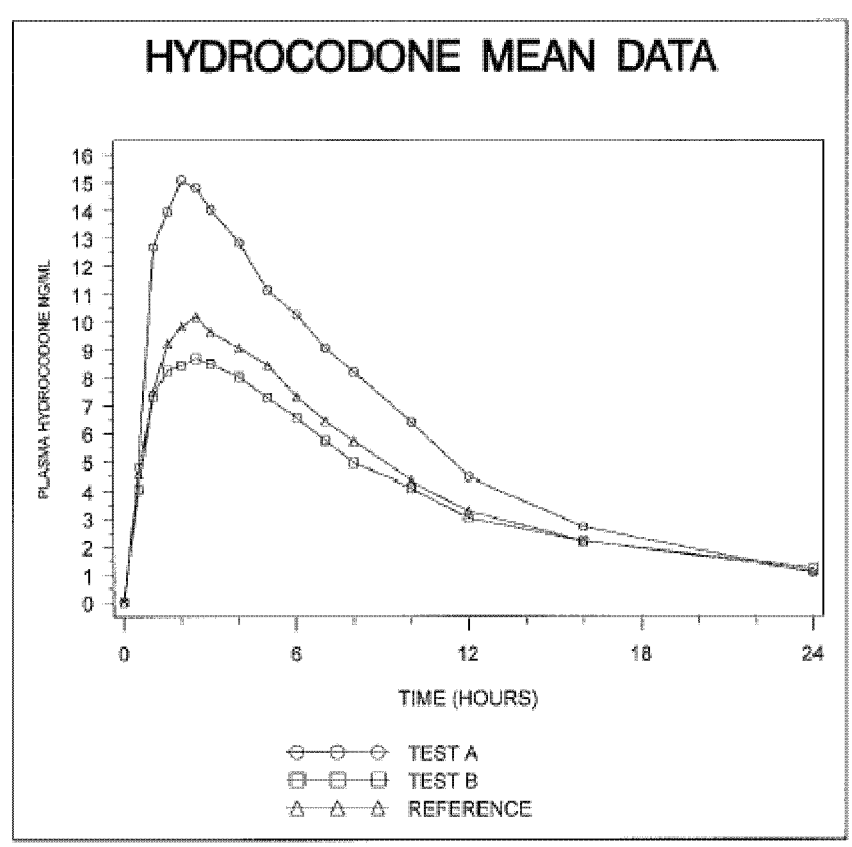
FIG. 11 shows in vivo serum concentration profiles for two batches of drug product comprising coated hydrocodone polistirex resins compared to an in vivo serum concentration for a Tussionex® drug suspension.
Figure 12:
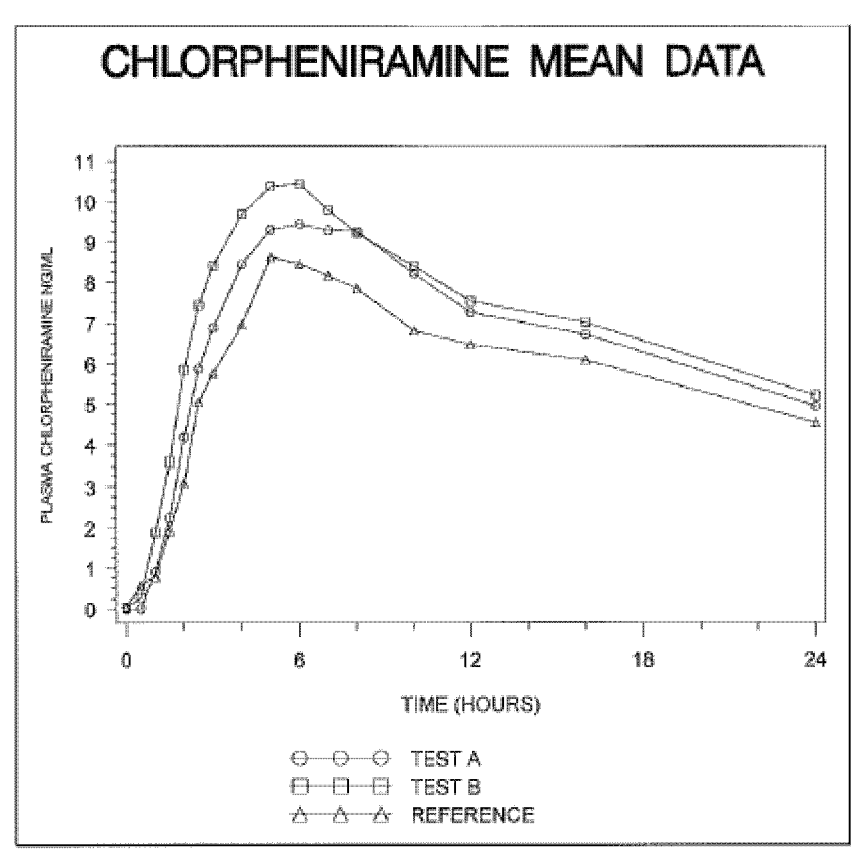
FIG. 12 shows in vivo serum concentration profiles for two batches of drug product comprising uncoated chlorpheniramine polistirex resins compared to an in vivo serum concentration for a Tussionex® drug suspension.

Plasma samples were taken at regular intervals and analyzed for the two active pharmaceutical ingredients and the plasma concentrations were plotted over time (see FIGS. 11 and 12).

The hydrocodone and chlorpheniramine plasma levels show a typical biological release profile. The clinical plasma concentration data, along with the dissolution release data in all four graphs can be correlated to each other for a predicable in vitro-in vivo relationship.

Figure 13:
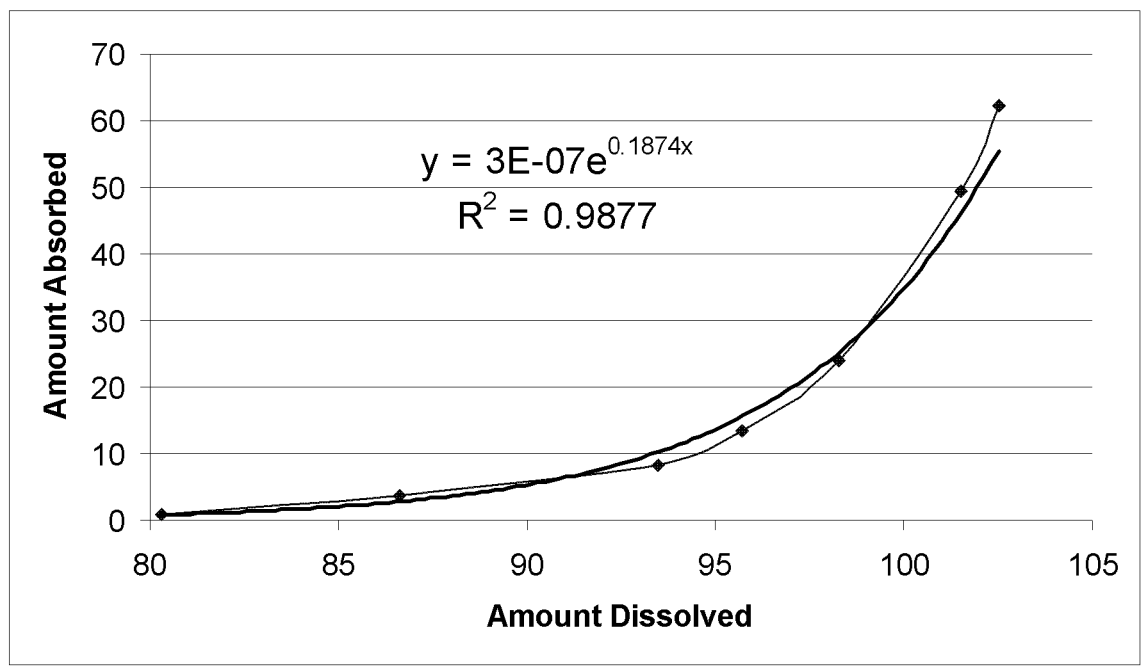
FIG. 13 shows an in vitro-in vivo correlation as described in Example 3.

C. Calculation of In Vitro-In Vivo Correlation of Coated Hydrocodone Polistirex And Chlorpheniramine Polistirex, Based Upon Dissolution Data and Clinical Plasma Data To find a correlation between the dissolution results and the clinical results for Lot A, these results were plotted together and a mathematical relationship was found. From the mean plasma concentration data from the clinical data, the area under the curve (AUC) as a function of time using the trapezoidal rule[1] was determined, and along with the knowledge of the elimination rate constant (Kel), then the calculation of Fa was possible[2]. Fa, the fraction of the dose absorbed is as follows in Equation 1:

[1] Edwards & Penney, "Calculus and Analytical Geometry, 4$^{th}$ Ed." Prentice-Hall Inc. 1994.
[2] Bourne, D. "A First Course in Pharmacokinetics and Biopharmaceutics—Chapter 9", University of Oklahoma, 2008.

$$F = \left(\frac{Kel \cdot V \cdot AUC}{Dose}\right)$$

with V being the Volume of the Dose (5 mL) and the "Dose" being 1×10$^7$ ng (10 mg) for the equivalent of 10 mg of hydrocodone bitartrate. The fraction of the dose was then converted into a cumulative percentage which was then plotted with the dissolution value. A Condition was then derived from that graph, creating an in vitro-in vivo correlation, which is shown in FIG. 13.

Therefore, the relationship between the dissolution value and physicochemical absorption rate was shown to be:
Equation 2—In Vitro-In Vivo Correlation of Hydrocodone:

$$Y = 3 \times 10^{-7} e^{0.1874x}$$

The correlation Coefficient value of 0.9877 shows a very good correlation of the exponential and the actual data values.

Similarly the in vitro-in vivo correlation of Lot B and Tussionex® drug suspension then becomes equation 3 and 4, respectively.
Equation 3—In Vitro-In Vivo Correlation of Hydrocodone in Lot B:

$$Y = 2 \times 10^{-6} e^{0.2641x}$$

$$R^2 = 0.9823$$

Equation 4—In Vitro-In Vivo Correlation of Hydrocodone in Branded Tussionex® Drug Suspension:

$$Y = 7 \times 10^{-5} e^{0.1969x}$$

$$R^2 = 0.9833$$

For similar in vitro-in vivo correlation guidance published by the Environmental Protection Agency (EPA) for acute toxicity determination,[3] the $R^2$ that is cited of 0.775 is characterized as "shows a significant comparability of data". A successful correlation is published as having a correlation coefficient >0.9[4]. Therefore, it was concluded that a correlation coefficient of >0.98 is very promising for the coated hydrocodone polistirex.

[3] "Guidance Document on Using In vitro Data to Estimate In Vivo Starting Doses for Acute Toxicity". Interagency Coordinating Committee on the Validation of Alternative Methods and the National Institute of Environmental Health Services; NIH Pub. No. 01-4500; August, 2001.
[4] Polli, J. E. "IVIVR versus IVIVC", Diss. Tech. Vol. 7, Issue 3; August 2000

The chlorpheniramine in vitro-in vivo correlations were less predictable, with $R^2$<0.75 for Lot A and B, and only 0.88 for the branded Tussionex® drug suspension. This was not entirely unexpected. The chlorpheniramine polistirex is considered an enterically immediate release dosage form, due to the pH dependent release mechanism of the drug, as can be seen in FIG. 10 after the 1 hour pH addition. There is generally a low expectation for the IVIVC success for immediate release dosages, and so it is not considered appropriate to use a correlation to compare dissolution and clinical data sets.

Figure 14:
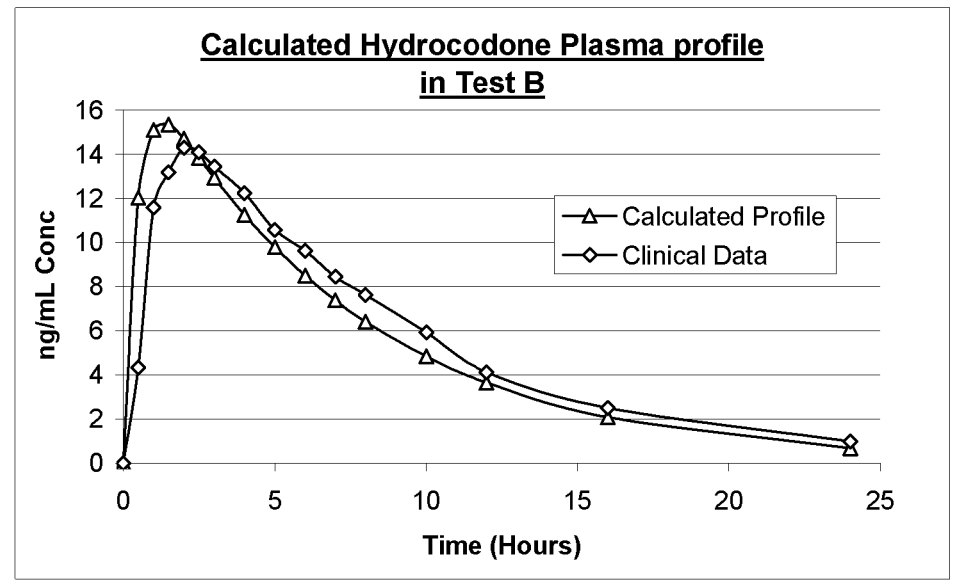
FIG. 14 shows a mathematical model for the plasma absorption of the specified dosage form of coated hydrocodone polistirex using the Wager-Nelson method.

Along with an IVIVC, other useful information may be obtained. Using the Wager-Nelson method, the absorption rate constant (Ka) can be calculated for the coated hydrocodone polistirex, since Kel is known, and with this constant a pure mathematical model can be created for the plasma absorption of the specified dosage form, see equation 5 and FIG. 14. Therefore, a model can be used in creating a predictive mode for bioavailability and bioequivalence of future products.
Equation 5:

$$\text{Plasma Conc.} = A[e^{-kel^*t} - e^{-ka^*t}]$$

Therefore, the plasma absorption concentration becomes the difference between the Kel rate and the Ka rate.

Conclusion

Although a non-linear IVIVC is fairly rare in literature, it is still a good predictor of a relationship between clinical and dissolution data. The correlation obtained according to the method of this invention is still considered to meet the Level A regulatory guidance set forth by the FDA. Therefore, the IVIVC described in this evaluation for coated hydrocodone polistirex can serve as a surrogate for in viva bioavailability and possible support of biowaivers in future therapeutic products submitted for ANDAs and NDAs. These models can also assist in the creation of future developmental dosages, scale-up and quality control changes throughout the manufacturing of the product life cycle.

Example 4

Time-Dependent Change in Release Behavior

It was noticed that when ethylcellulose coated hydrocodone polistirex resita was formulated in a Drug Product matrix as in Example 3, the dissolution profile of hydrocodone release changed over time. This change constituted an increase in the released amount of drug product over all dissolution time points. After about three to four weeks of room temperature storage, the release profile ceased shifting and remained stable over the remaining shelf-life of the Drug Product. Without wishing to be bound by theory, this phenomenon was theorized to be a caused by changes in the coated hydrocodone polistirex resin within the Drug Product matrix to approach a thermodynamically stable equilibrium in the formulated suspension.

Figure 15:
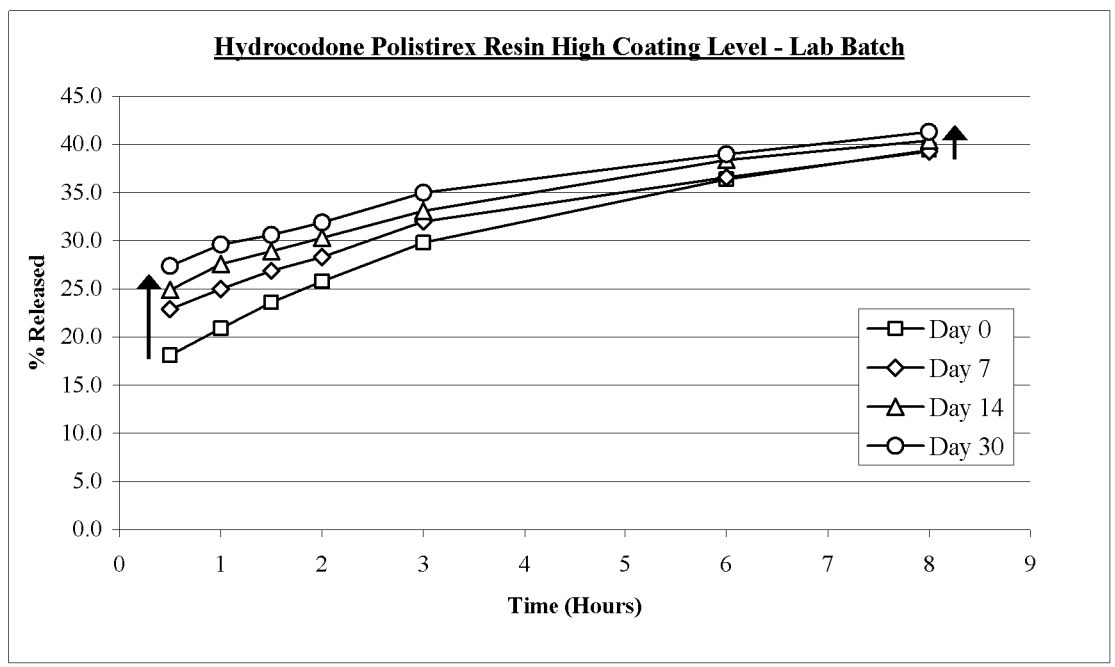
FIG. 15 shows a graphical representation of changes in drug products release profiles over time measured from completion of final suspension with a high coating level.
Figure 16:
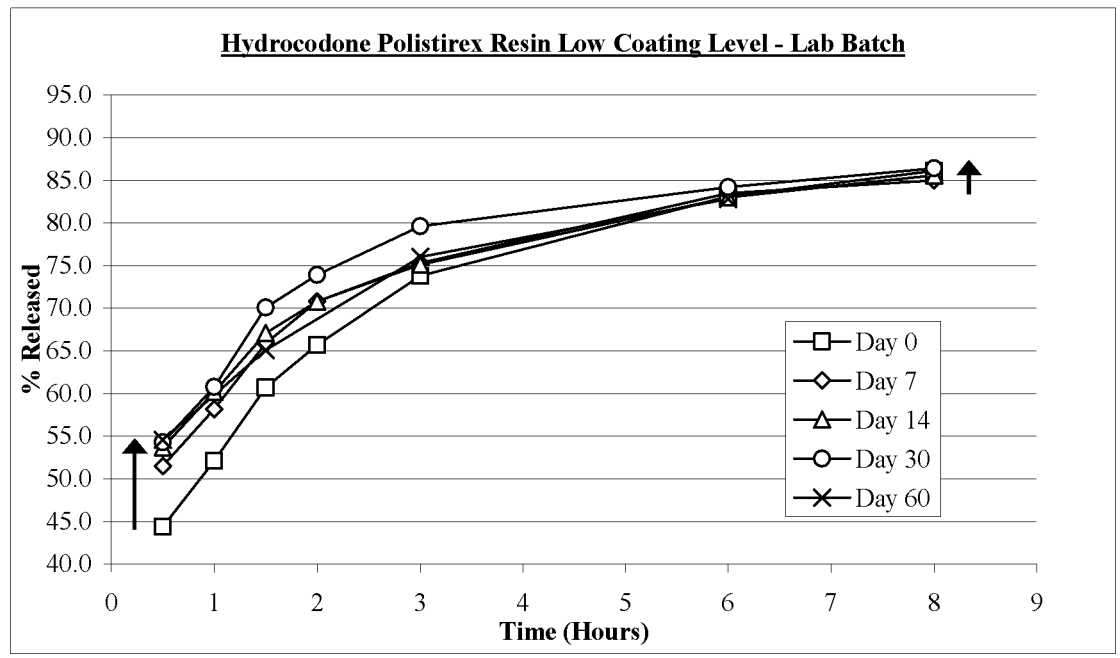
FIG. 16 shows a graphical representation of changes in drug products release profiles over time measured from completion of final suspension with a low coating level.

Coating levels of the hydrocodone polistirex resinate did not seem to appreciably affect the equilibrium shift of the release profile. Laboratory batches were made using the same two coating level hydrocodone polistirex resinates that were used to manufacture the batches used in Example 2. The change in the hydrocodone in-vitro drug release, as measured with the protocol described in Example 3, for both laboratory batches, regardless of the coating level, showed a similar equilibrium shift after various periods of storage at room temperature (FIGS. 15 and 16).

The equilibrium shift, from day 0 to day 30 at the 30 minute time point was 9.3% for the laboratory batch manufactured using the higher coating level material and 9.9% for the laboratory batch manufactured using the lower coating level material. The equilibrium shift, from day 0 to day 30 at the 8 hour time point was 2.0% for the laboratory batch manufactured using the higher coating level material and 1.4% for the laboratory batch manufactured using the lower coating level material. These amounts are very similar, with the difference in equivalence shift being less than 1%, even though the dissolution release profiles are significantly different. FIGS. 15 and 16 demonstrate a graphical representation of changes in the Drug Products release profile over time measured from completion of final suspension with the two different coating levels described above.

Figure 17:
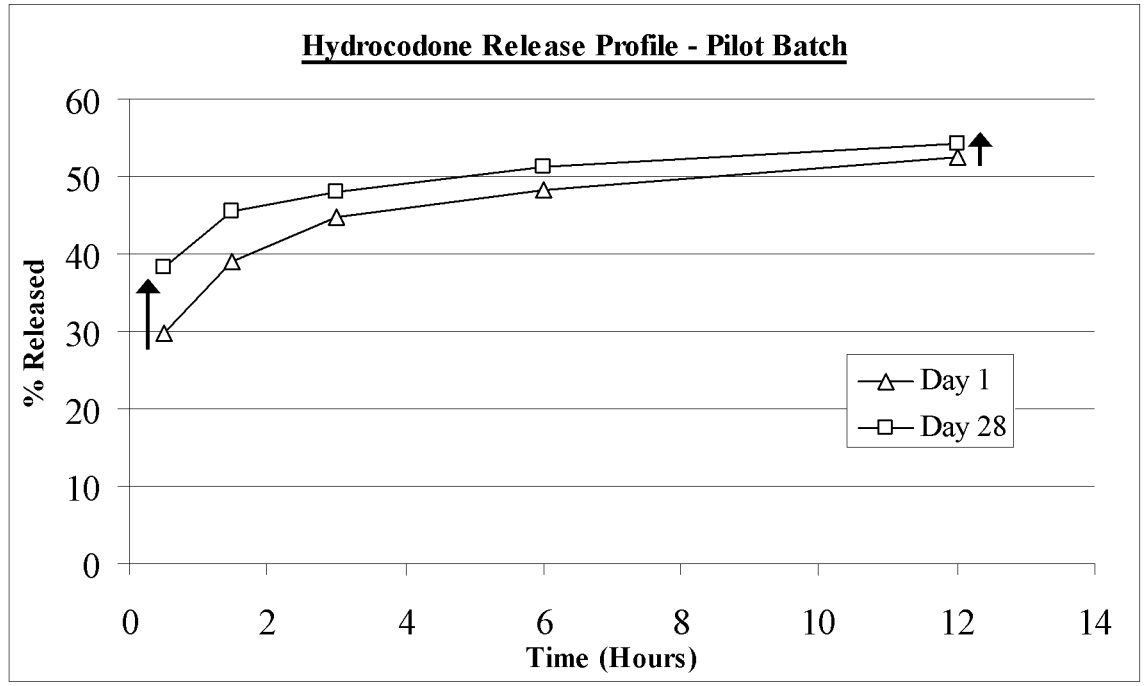
FIG. 17 shows a graphical representation of the equilibrium shift over the 28 day equilibration period in a suspension of hydrocodone polistirex resin and chlorpheniramine polistirex resin.

A 300 Liter Pilot Batch hydrocodone equilibrium shift over the 28 day equilibrium period (results in FIG. 17) was similar to the previously seen equilibrium shifts. The initial dissolution time point had a shift of 8.5%, while the 6 hour time point resulted in a shift of 3.0%.

Example 5

Effect of Heating During Suspension Manufacture

Experiments were performed in an attempt to accelerate the equilibrium process. Product was prepared and stored as in Example 4 except that it was manufactured at 50° C.

The first experiment performed in an attempt to accelerate the equilibrium process involved heating the Drug Product during the manufacturing process. This experiment was selected after reviewing Free Energy calculations and Gibbs Law[5]. Gibbs free energy ΔG is the work exchanged by the system with its surroundings, during a reversible transformation of the system from some specified initial state to a final state.

[5] General Chemistry, Principles and Structures 3rd Edition, J. E. Brandy and G. E. Hurniston; John Wiley & Sons 1982.

$$\Delta G = \Delta H - T\Delta S$$

where G is the Free Energy, H is the Standard Enthalpy, S is the Entropy of the system, and T is the Temperature of the system.

If the ΔG becomes zero, then the system is at equilibrium. Due to the fact that the hydrocodone dissolution profile takes four weeks to reach equilibrium, the reaction would be considered non-spontaneous. This results in a positive ΔG. Therefore, in order to decrease ΔG to zero, the term TΔS must be increased.

Figure 18:
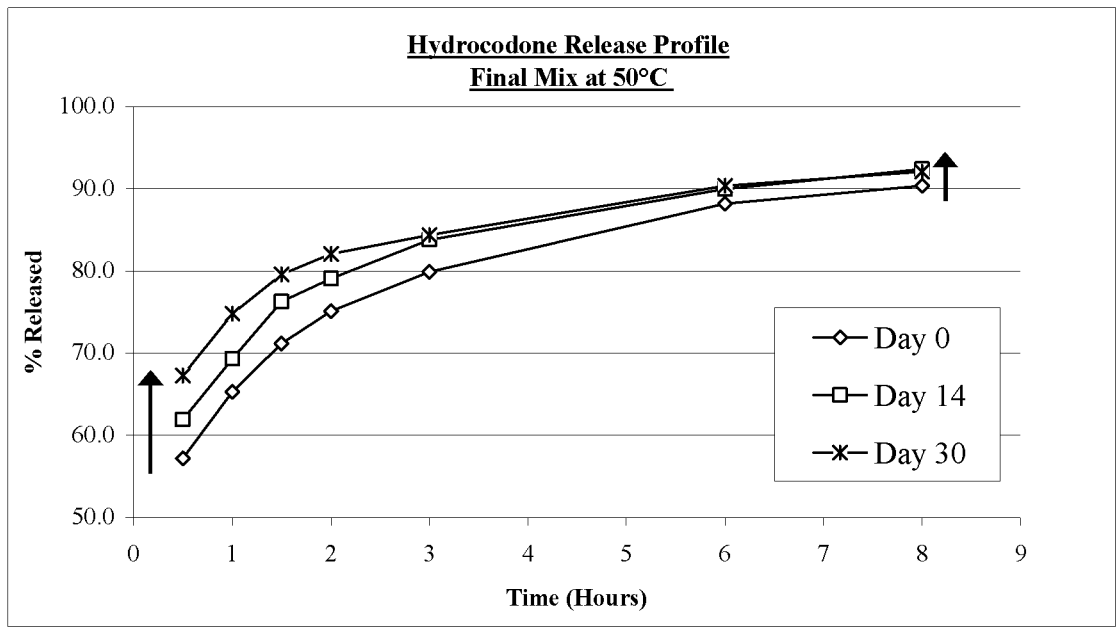
FIG. 18 shows a graphical representation of the equilibrium shift of a drug product that was prepared and stored at 50° C.

The heating of the Drug Product during manufacturing did not reduce the equilibrium time (results in FIG. 18). The final equilibrium results showed an equilibrium shift of 10.1% for the first dissolution time point, decreasing to 2.0% for the final dissolution time point. This is similar to previously seen equilibrium shifts over four weeks. As a result of the heating, the final hydrocodone dissolution profile started and ended with a higher release profile than the non-heated samples.

The conclusion from this is that heating during the manufacturing process may affect the resin coating, which may cause the hydrocodone release profile to deviate from the predetermined desired rate. Various heating experiments involved heating batches at 40° C. and 50° C. as well as additional periods of mixing at the end of the process followed by room temperature storage. All of these experiments resulted in the same finding—the equilibrium time was not reduced.

Example 6

Effect of pH

Figure 19:
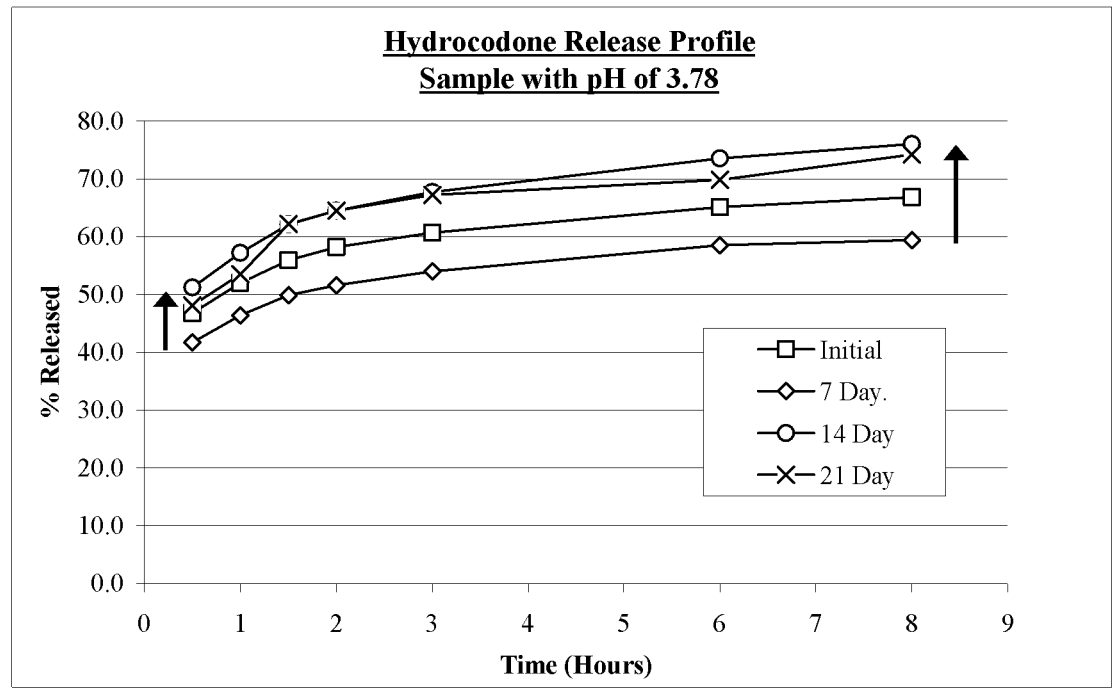
FIG. 19 shows a graphical representation of the equilibrium shift of a drug product at different pH levels.

Due to the ion exchange nature of the hydrocodone polistirex resin, different pH levels of the Drug Product were evaluated as a means of accelerating the equilibrium process. The first experiment was carried out as described in Example 4 except for lowering the pH of the Drug Product with an excess of Ascorbic Acid (results in FIG. 19). The initial dissolution time point had a shift of 9.5%, which is in accordance with batches at the target pH of approximately 4.2. The final dissolution time point at 8 hours had a shift of 16.6%, which was larger than what was previously seen. This experiment included two other batches of Drug Product, one at the target pH and another that was made without Ascorbic Acid in order to achieve a high pH level. These batches demonstrated the same equilibrium shift as the batch manufactured with the low pH.

All of these experiments resulted in the same finding—the equilibrium time was not reduced, in fact the results were all very similar. The pH adjustments were made at the end of the process (as opposed to the beginning of the process which is how this Drug Product is typically prepared).

Example 7

Effect of the Removal of Chlorpheniramine Polistirex Resin

Figure 20:
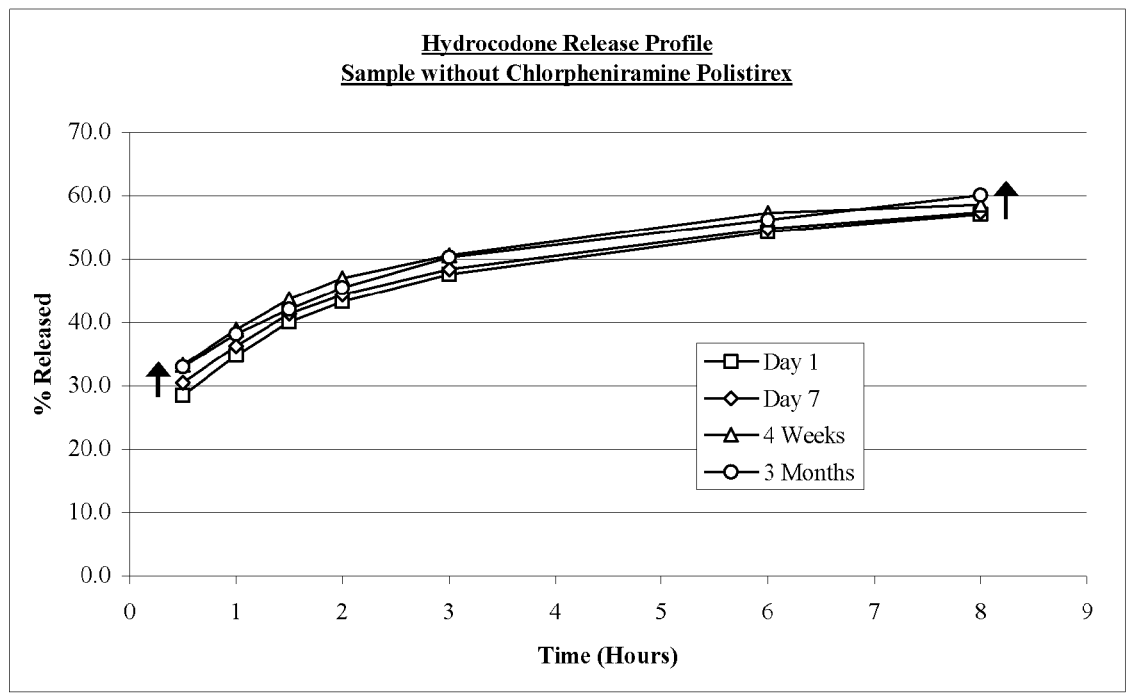
FIG. 20 shows a graphical representation of the equilibrium shift of a drug product that contains hydrocodone polistirex resin, but does not contain chlorpheniramine polistirex resin.

A suspension containing only hydrocodone polistirex resin was prepared to determine whether the chlorpheniramine polistirex resin had an affect on the equilibrium shift of the hydrocodone dissolution release profile. This experiment was carried out as in Example 3 except for omitting chlorpheniramine polistirex resin. Results are shown in FIG. 20. The initial dissolution time point had a shift of 4.5%, which is approximately half the value seen on similar batches. The final dissolution time point at 8 hours had a shift of 2.7%, which is similar to previously seen shifts. This decrease in an equilibrium shift seems to be due to the absence of chlorpheniramine polistirex resin. Thus, the presence of polistirex resin which does not have bound hydrocodone appears to affect the equilibrium shift. This result is consistent with the need to determine release profiles using drug-resin particles which are formulated in a suspension substantially similar to the final formulation as defined herein in order to obtain an in infra release profile which can be used to predict the IVIVC of the final suspended product.

Example 8

Profile Comparison of Particles Tested in the Final Drug Suspension

The invention provides for methods of characterizing drug-containing resin particles to determine if they meet particular quality parameters. The method includes the steps of suspending drug-containing resin particles in a test suspension that is substantially similar in physicochemical characteristics to a final drug suspension, such as that described in Example 3, and producing an in vitro dissolution profile obtained from the test suspension using a suitable dissolution protocol, such as that described in Example 3. Drug-containing resin particles may be accepted or rejected based on this dissolution profile.

In this Example, release profiles of drug-containing resin particles treated in different ways were compared using the protocol described in Example 3. In particular, the release profiles of hydrocodone resins having low and high coating weights were placed in a drug suspension described in Example 3, and aliquots of the drug suspension were assayed in the dissolution protocol of Example 3 after one day of storage. The resulting profiles were compared with the release profiles of hydrocodone resin particles having low and high coating weights that were not prepared in a drug suspension, but rather were introduced directly into the dissolution medium of Example 3 (i.e., as dry coated particles).

Figure 21:
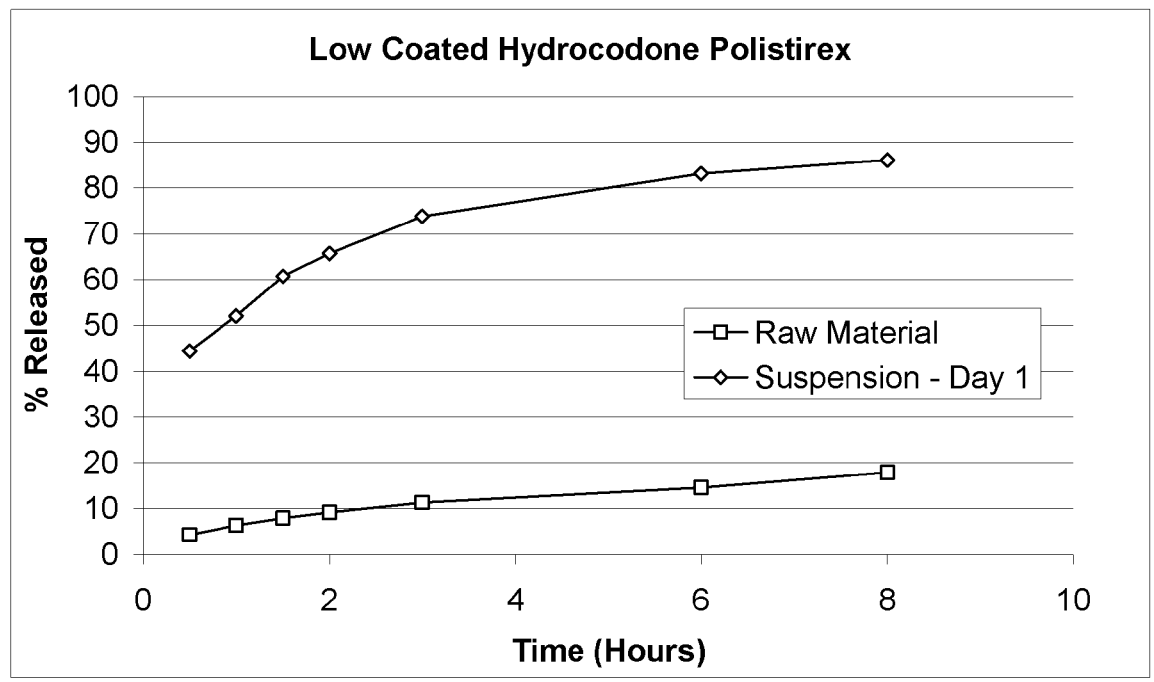
FIG. 21 shows release profiles of (a) a hydrocodone resin with a high coating weight when prepared in a drug suspension substantially similar to a final drug suspension ("Suspension—Day 1"), and (b) the hydrocodone resin by itself ("Raw Material"), tested using the same dissolution test methods as the finished product, but without first suspending it in a drug suspension.
Figure 22:
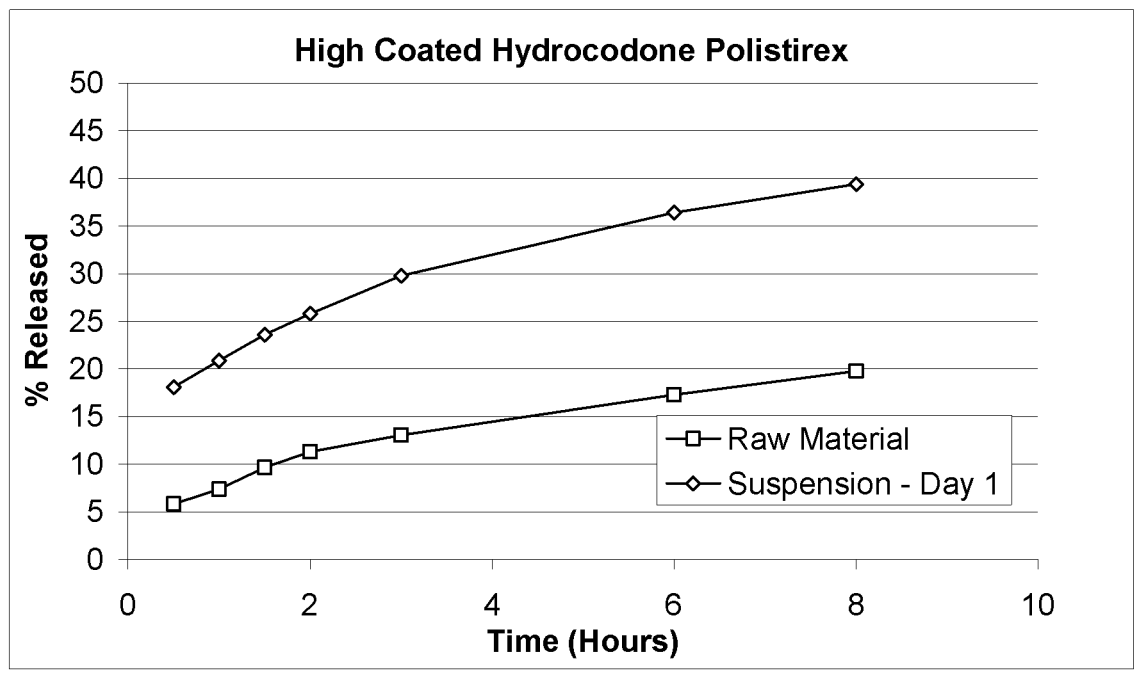
FIG. 22 shows release profiles of (a) a hydrocodone resin with a low coating weight when prepared in a drug suspension substantially similar to a final drug suspension ("Suspension—Day 1"), and (b) the hydrocodone resin by itself, tested using the same dissolution test methods as the finished product, but without first suspending it in a drug suspension ("Raw Material").

The top line in FIGS. 21 and 22 is the release profile of the hydrocodone resin when prepared in a drug suspension substantially similar to a final drug suspension ("Suspension—Day 1"), and the lower line is the release profile of the hydrocodone resin by itself, tested using the same dissolution test methods as the finished product (same dissolution and HPLC settings), but without first suspending it in a drug suspension substantially similar to a final drug suspension. The lower line of both figures shows a similar profile, indicating that dissolution assays on dry particles are not sensitive to the differences between the particle populations. On the other hand, after one day in suspension, the release profiles of the two population of particles reflects the effect of coating weight expected from the results in Examples 2, 3, and 4.

This example demonstrates that the release profiles of liquid drug suspensions comprising drug-resin particles may be used to evaluate the release performance expected for loaded resin particles when prepared in a drug suspension substantially similar to a final drug suspension. However, if the loaded resin particles are tested directly, without formulation into a suspension, the release performance is changed. Using the method of this invention one can test the acceptability of a drug-containing resin particle without having to wait for a final product to be formulated and fully aged, thereby saving time and expense during the production process. Of course, the release profile after one day does not match the in vitro profile of a fully aged suspension, but the profile after a preselected storage period can be correlated to the in vitro portion of an IVIVC for purposes of prediction.

Example 9

Modifying Particle Size and Distribution

Particle size is investigated in this Example by looking at two parameters, particle size distribution and the actual particle size of a coated hydrocodone-containing resinate. Coated hydrocodone polistirex is the only component assayed for drug release in this set of studies. As the chlorpheniramine polistirex release mechanism is purely ion and pH related (due to the lack of coating) release rate for chlorpheniramine is not expected to be dependent upon particle size.

Coated hydrocodone polistirex from a bulk sample was separated into various particle size ranges. A large 250 gram composite sample of hydrocodone polistirex was sieved through six U.S Standard Test Sieves. The percent weight distribution and percent assay equivalent to hydrocodone bitartrate that were determined are outlined in Table 3 below as follows. The assay value of hydrocodone equivalent to hydrocodone bitartrate on a percent weight basis is fairly uniform throughout the particles, with a relative variation of approximately 8%. As can be seen in the percent weight retained column, the majority of the sample has a particle size between 75 μm and 149 μm.

TABLE 3

Particle Size Separation and Analysis

| Sieve Size (Particle size) | Weight Retained | Hydrocodone Assay (% w/w) |
|---|---|---|
| USS 60 (>250 μm) | 2.1% | 15.2 |
| USS 80 (180 to 249 μm) | 11.1% | |
| USS 100 (150 to 179 μm) | 7.9% | 16.1 |
| USS 120 (125 to 149 μm) | 21.5% | 16.2 |
| USS 140 (106 to 124 μm) | 20.7% | 16.1 |
| USS 200 (75 to 105 μm) | 22.3% | 15.3 |
| Pan Sample (<75 μm) | 14.3% | 15.0 |
| Loss | 0.1% | |
| Total | 100.0% | |

Figure 23:
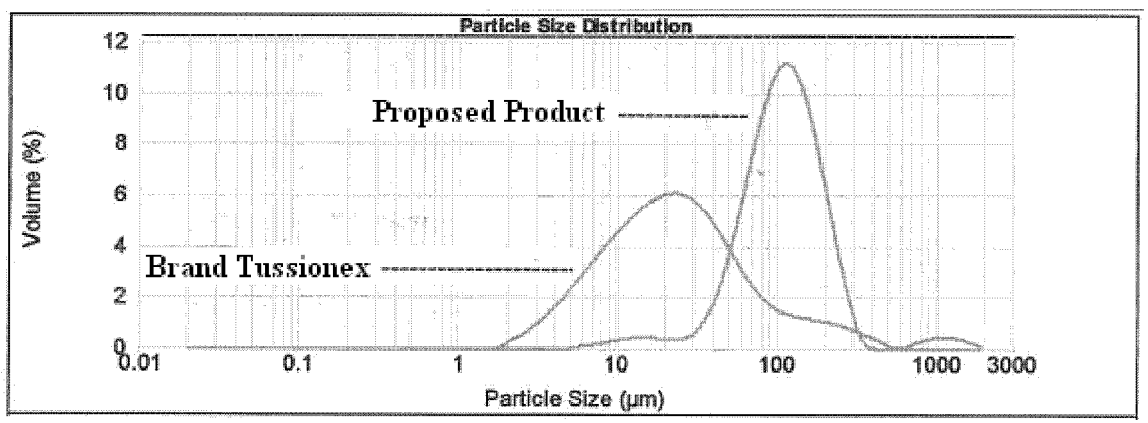
FIG. 23 shows a graphical representation of the percent volume of two samples (i.e., the particle size distribution), as measured using light scatter diffraction. One sample is commercial Tussionex®; the other sample is a product formulated as described in Example 3.
Figure 24:
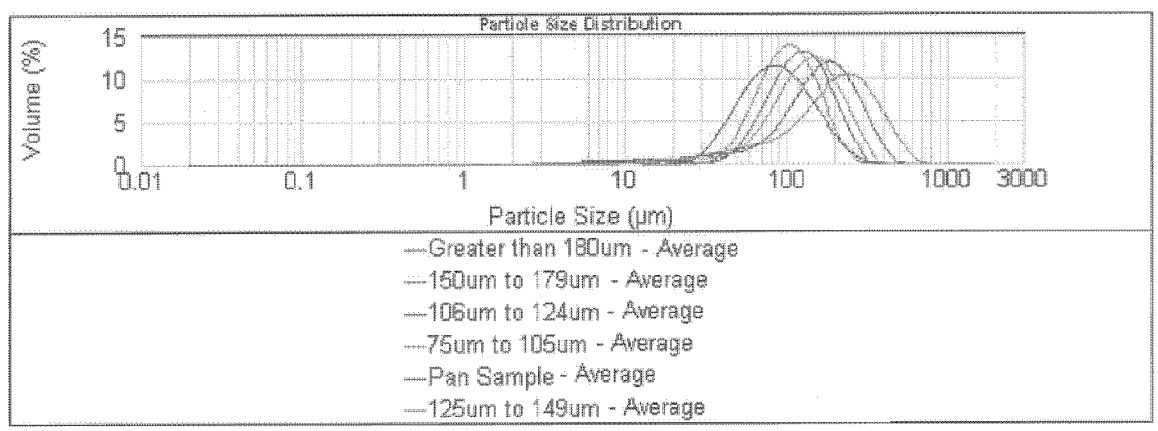
FIG. 24 shows a graphical representation of the percent volume of each individual fraction (i.e., the particle size distribution), as measured using light scatter diffraction, for six fractions of a product formulated as described in Example 3.

The percent volume of the composite sample (i.e., the product described in Example 3 and referred to as "proposed product"), as measured using light scatter diffraction and displayed in FIG. 23 and Table 4 that follow, exhibited a similar distribution to the data obtained using sieve analysis displayed in the Table 3 above.

TABLE 4

| | Particle size d0.1 [The size of the particle in microns below which 10% (on a volume basis) of the sample lies.] | Particle size d0.5 [The size of the particle in microns at which 50% of the sample is smaller and 50% is larger.] | Particle size d0.9 [The size of the particle in microns below which 90% of the sample lies.] |
|---|---|---|---|
| Reference Listed Drug | 6 μm | 22 μm | 95 μm |
| Proposed Product | 30 μm | 100 μm | 200 μm |

The percent volume of each individual sample, as measured using light scatter diffraction and displayed in the FIG.

24, also exhibited similar distribution to the data obtained using sieve analysis displayed in the Table 4 above.

This experiment shows that coated hydrocodone polistirex which produces release data bioequivalent to Tussionex® drug suspension may be prepared with particle size distribution shifted toward larger particles (>50 μm). Such particles may be used to prepare drug suspensions without requiring milling of the resin particles. Dissolution studies indicate that narrower ranges of particle size may be used to enhance release characteristics. Suspensions with narrower ranges of particle size may produce more consistent release profiles.

All documents (e.g., patents and published patent applications) mentioned in this specification are hereby incorporated by reference in their entirety.

The invention claimed is:

1. A pharmaceutical composition comprising (a) hydrocodone polistirex particles coated with a semi-permeable membrane, (b) chlorpheniramine polistirex particles, and (c) at least one liquid carrier,
wherein at least 50% of all the polistirex particles are larger than 50 μm, and further wherein said composition is suitable for commercial distribution.

2. The pharmaceutical composition of claim 1, wherein hydrocodone content is equivalent to 10 mg of hydrocodone bitartrate in a pharmaceutically acceptable dose.

3. The pharmaceutical composition of claim 2, wherein the pharmaceutically acceptable dose is 5-15 milliliters.

4. The pharmaceutical composition of claim 1, wherein chlorpheniramine content is equivalent to 8 mg of chlorpheniramine maleate in a pharmaceutically acceptable dose.

5. The pharmaceutical composition of claim 4, wherein the pharmaceutically acceptable dose is 5-15 milliliters.

6. The pharmaceutical composition of claim 1, wherein the semi-permeable membrane comprises ethylcellulose.

7. The pharmaceutical composition of claim 1, wherein the liquid carrier is aqueous based and contains one or more suspending agents.

8. The pharmaceutical composition of claim 1, wherein at least 80% of all the polistirex particles are smaller than 500 μm.

9. The pharmaceutical composition of claim 1, wherein at least 80% of all the polistirex particles are smaller than 200 μm.

10. A pharmaceutical composition comprising (a) hydrocodone polistirex particles coated with a semi-permeable membrane, (b) chlorpheniramine polistirex particles, and (c) at least one liquid carrier,
wherein at least 50% of the coated polistirex particles are larger than 50 μm, and further wherein said composition is suitable for commercial distribution.

11. The pharmaceutical composition of claim 10, wherein hydrocodone content is equivalent to 10 mg of hydrocodone bitartrate in a pharmaceutically acceptable dose.

12. The pharmaceutical composition of claim 11, wherein the pharmaceutically acceptable dose is 5-15 milliliters.

13. The pharmaceutical composition of claim 10, wherein chlorpheniramine content is equivalent to 8 mg of chlorpheniramine maleate in a pharmaceutically acceptable dose.

14. The pharmaceutical composition of claim 13, wherein the pharmaceutically acceptable dose is 5-15 milliliters.

15. The pharmaceutical composition of claim 10, wherein the semi-permeable membrane comprises ethylcellulose.

16. The pharmaceutical composition of claim 10, wherein the liquid carrier is aqueous based and contains one or more suspending agents.

17. The pharmaceutical composition of claim 10, wherein at least 80% of the coated polistirex particles are smaller than 500 μm.

18. The pharmaceutical composition of claim 10, wherein at least 80% of the coated polistirex particles are smaller than 200 μm.

* * * * *